United States Patent
Koop et al.

(10) Patent No.: US 11,123,570 B2
(45) Date of Patent: *Sep. 21, 2021

(54) IMPLANTABLE MEDICAL DEVICE FOR VASCULAR DEPLOYMENT

(71) Applicant: CARDIAC PACEMAKERS, INC., St. Paul, MN (US)

(72) Inventors: Brendan Early Koop, Ham Lake, MN (US); Benjamin J. Haasl, Forest Lake, MN (US); Allan Charles Shuros, St. Paul, MN (US); James O. Gilkerson, Stillwater, MN (US); Lili Liu, Maple Grove, MN (US); Keith R. Maile, New Brighton, MN (US); Brian Soltis, St. Paul, MN (US); Brandon Christopher Fellows, Chicago, IL (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 191 days.

This patent is subject to a terminal disclaimer.

(21) Appl. No.: 16/225,570

(22) Filed: Dec. 19, 2018

(65) Prior Publication Data

US 2019/0192864 A1  Jun. 27, 2019

Related U.S. Application Data

(60) Provisional application No. 62/609,565, filed on Dec. 22, 2017.

(51) Int. Cl.
*A61N 1/375* (2006.01)
*A61M 25/01* (2006.01)
(Continued)

(52) U.S. Cl.
CPC ........ *A61N 1/3756* (2013.01); *A61B 17/3468* (2013.01); *A61M 25/0147* (2013.01);
(Continued)

(58) Field of Classification Search
CPC .. A61N 1/3756; A61N 1/37518; A61N 1/056; A61N 1/057; A61N 1/368;
(Continued)

(56) References Cited

U.S. PATENT DOCUMENTS

| 5,170,802 A | 12/1992 | Mehra |
| 5,238,004 A | 8/1993 | Sahatjian et al. |

(Continued)

FOREIGN PATENT DOCUMENTS

| EP | 2769750 A1 | 8/2014 |
| WO | 2008070120 A2 | 6/2008 |

(Continued)

OTHER PUBLICATIONS

International Search Report and Written Opinion dated Mar. 28, 2019 for International Application No. PCT/US2018/066447.

*Primary Examiner* — Allen Porter
(74) *Attorney, Agent, or Firm* — Seager, Tufte & Wickhem LLP

(57) ABSTRACT

A leadless pacing device may include a housing having a proximal end and a distal end, and a set of one or more electrodes supported by the housing. The housing may include a first a distal extension extending distally from the distal end thereof. The distal extension may include a retractable and/or rotatable distal electrode. The distal electrode may be configured to be delivered to and pace at the Bundle of His. The leadless pacing device may be releasably coupled to an expandable anchor mechanism.

20 Claims, 13 Drawing Sheets

(51) Int. Cl.
*A61B 17/34* (2006.01)
*A61N 1/05* (2006.01)
*A61N 1/368* (2006.01)
*A61N 1/372* (2006.01)
*A61N 1/365* (2006.01)

(52) U.S. Cl.
CPC ......... *A61N 1/057* (2013.01); *A61N 1/37512* (2017.08); *A61N 1/37516* (2017.08); *A61N 1/056* (2013.01); *A61N 1/365* (2013.01); *A61N 1/368* (2013.01); *A61N 1/37288* (2013.01); *A61N 1/37518* (2017.08); *A61N 2001/058* (2013.01)

(58) Field of Classification Search
CPC ............ A61N 1/37512; A61N 1/37516; A61B 17/3468; A61M 25/0147
See application file for complete search history.

(56) References Cited

U.S. PATENT DOCUMENTS

| | | | |
|---|---|---|---|
| 5,540,236 A | 7/1996 | Ginn | |
| 5,803,928 A | 9/1998 | Tockman et al. | |
| 5,925,073 A | 7/1999 | Chastain et al. | |
| 6,070,104 A | 5/2000 | Hine et al. | |
| 6,416,474 B1 | 7/2002 | Penner et al. | |
| 6,442,413 B1 | 8/2002 | Silver | |
| 6,445,953 B1 | 9/2002 | Bulkes et al. | |
| 6,508,803 B1 | 1/2003 | Horikawa et al. | |
| 6,584,362 B1 | 6/2003 | Scheiner et al. | |
| 6,592,518 B2 | 7/2003 | Denker et al. | |
| 6,783,499 B2 | 8/2004 | Schwartz | |
| 6,907,285 B2 | 6/2005 | Denker et al. | |
| 7,003,350 B2 | 2/2006 | Denker et al. | |
| 7,082,336 B2 | 7/2006 | Ransbury et al. | |
| 7,164,852 B2 | 1/2007 | Cazzini et al. | |
| 7,236,821 B2 | 6/2007 | Cates et al. | |
| 7,295,879 B2 | 11/2007 | Denker et al. | |
| 7,309,354 B2 | 12/2007 | Mathis et al. | |
| 7,310,556 B2 | 12/2007 | Bulkes | |
| 7,519,421 B2 | 4/2009 | Denker et al. | |
| 7,529,589 B2 | 5/2009 | Williams et al. | |
| 7,535,296 B2 | 5/2009 | Bulkes et al. | |
| 7,572,228 B2 | 8/2009 | Wolinsky et al. | |
| 7,617,007 B2 | 11/2009 | Williams et al. | |
| 7,711,434 B2 | 5/2010 | Denker et al. | |
| 7,734,343 B2 | 6/2010 | Ransbury et al. | |
| 7,749,265 B2 | 7/2010 | Denker et al. | |
| 7,769,466 B2 | 8/2010 | Denker et al. | |
| 7,801,626 B2 | 9/2010 | Moser | |
| 7,826,903 B2 | 11/2010 | Denker et al. | |
| 7,840,282 B2 | 11/2010 | Williams et al. | |
| 7,894,915 B1 | 2/2011 | Chitre et al. | |
| 7,899,554 B2 | 3/2011 | Williams et al. | |
| 8,050,775 B2 | 11/2011 | Westlund et al. | |
| 8,103,359 B2 | 1/2012 | Reddy | |
| 8,116,883 B2 | 2/2012 | Williams et al. | |
| 8,160,722 B2 | 4/2012 | Rutten et al. | |
| 8,204,596 B2 | 6/2012 | Ransbury et al. | |
| 8,239,045 B2 | 8/2012 | Ransbury et al. | |
| 8,311,633 B2 | 11/2012 | Ransbury et al. | |
| 8,489,205 B2 | 7/2013 | Stotts et al. | |
| 8,527,068 B2 | 9/2013 | Ostroff | |
| 8,571,678 B2 | 10/2013 | Wang | |
| 8,630,710 B2 | 1/2014 | Kumar et al. | |
| 8,634,912 B2 | 1/2014 | Bornzin et al. | |
| 8,634,919 B1 | 1/2014 | Hou et al. | |
| 8,644,934 B2 | 2/2014 | Hastings et al. | |
| 8,670,824 B2 | 3/2014 | Anderson et al. | |
| 8,670,842 B1 | 3/2014 | Bornzin et al. | |
| 8,700,181 B2 | 4/2014 | Bornzin et al. | |
| 8,727,996 B2 | 5/2014 | Allan et al. | |
| 8,758,365 B2 | 6/2014 | Bonner et al. | |
| 8,781,605 B2 | 7/2014 | Bornzin et al. | |
| 8,798,740 B2 | 8/2014 | Samade et al. | |
| 8,798,770 B2 | 8/2014 | Reddy | |
| 8,886,340 B2 | 11/2014 | Williams et al. | |
| 8,914,131 B2 | 12/2014 | Bornzin et al. | |
| 8,938,294 B2 | 1/2015 | Anderson et al. | |
| 8,989,873 B2 | 3/2015 | Locsin | |
| 8,996,109 B2 | 3/2015 | Karst et al. | |
| 9,008,777 B2 | 4/2015 | Dianaty et al. | |
| 9,168,372 B2 | 10/2015 | Fain | |
| 9,204,842 B2 | 12/2015 | Mothilal et al. | |
| 9,265,962 B2 | 2/2016 | Dianaty et al. | |
| 9,278,218 B2 | 3/2016 | Karst et al. | |
| 9,289,612 B1 | 3/2016 | Sambelashvili et al. | |
| 9,339,197 B2 | 5/2016 | Griswold et al. | |
| 9,339,646 B2 | 5/2016 | Ollivier | |
| 9,399,140 B2 | 7/2016 | Cho et al. | |
| 9,446,248 B2 | 9/2016 | Sheldon et al. | |
| 9,468,755 B2 | 10/2016 | Westlund et al. | |
| 9,526,891 B2 | 12/2016 | Eggen et al. | |
| 9,539,423 B2 | 1/2017 | Bonner et al. | |
| 9,623,234 B2 | 4/2017 | Anderson | |
| 9,669,223 B2 | 6/2017 | Auricchio et al. | |
| 9,717,421 B2 | 8/2017 | Griswold et al. | |
| 9,814,896 B2 | 11/2017 | Solem | |
| 9,827,426 B2 | 11/2017 | Reddy | |
| 2004/0249417 A1* | 12/2004 | Ransbury et al. ...... A61N 1/375 607/4 |
| 2006/0122522 A1 | 6/2006 | Chavan et al. | |
| 2006/0241732 A1 | 10/2006 | Denker et al. | |
| 2007/0106357 A1 | 5/2007 | Denker et al. | |
| 2012/0029598 A1 | 2/2012 | Zhao | |
| 2012/0172690 A1 | 7/2012 | Anderson et al. | |
| 2012/0271134 A1 | 10/2012 | Allan et al. | |
| 2013/0023975 A1 | 1/2013 | Locsin | |
| 2013/0035636 A1 | 2/2013 | Beasley et al. | |
| 2013/0035748 A1 | 2/2013 | Bonner et al. | |
| 2013/0110127 A1 | 5/2013 | Bornzin et al. | |
| 2013/0110219 A1 | 5/2013 | Bornzin et al. | |
| 2013/0116529 A1 | 5/2013 | Min et al. | |
| 2013/0116738 A1 | 5/2013 | Samade et al. | |
| 2013/0116740 A1 | 5/2013 | Bornzin et al. | |
| 2013/0116741 A1 | 5/2013 | Bornzin et al. | |
| 2013/0123872 A1 | 5/2013 | Bornzin et al. | |
| 2013/0138006 A1 | 5/2013 | Bornzin et al. | |
| 2013/0253309 A1 | 9/2013 | Allan et al. | |
| 2013/0253342 A1 | 9/2013 | Griswold et al. | |
| 2013/0253346 A1 | 9/2013 | Griswold et al. | |
| 2013/0253347 A1 | 9/2013 | Griswold et al. | |
| 2013/0325081 A1 | 12/2013 | Karst et al. | |
| 2013/0345770 A1 | 12/2013 | Dianaty et al. | |
| 2014/0100627 A1 | 4/2014 | Min | |
| 2014/0107723 A1 | 4/2014 | Hou et al. | |
| 2014/0172034 A1 | 6/2014 | Bornzin et al. | |
| 2014/0172060 A1 | 6/2014 | Bornzin et al. | |
| 2014/0243848 A1 | 8/2014 | Auricchio et al. | |
| 2014/0257324 A1 | 9/2014 | Fain | |
| 2014/0288576 A1 | 9/2014 | Bornzin et al. | |
| 2016/0015287 A1 | 1/2016 | Anderson et al. | |
| 2016/0015322 A1 | 1/2016 | Anderson et al. | |
| 2016/0059003 A1 | 3/2016 | Eggen et al. | |
| 2016/0082270 A1 | 3/2016 | Mothilal et al. | |
| 2016/0129239 A1 | 5/2016 | Anderson | |
| 2016/0158561 A1 | 6/2016 | Reddy | |
| 2016/0228712 A1 | 8/2016 | Koop | |
| 2016/0310703 A1 | 10/2016 | Drake et al. | |
| 2016/0310723 A1 | 10/2016 | Eggen et al. | |
| 2016/0310726 A1 | 10/2016 | Demmer et al. | |
| 2017/0028194 A1 | 2/2017 | Bonner et al. | |
| 2017/0326355 A1 | 11/2017 | Koop et al. | |

FOREIGN PATENT DOCUMENTS

| | | |
|---|---|---|
| WO | 2016010958 A1 | 1/2016 |
| WO | 2016011042 A1 | 1/2016 |
| WO | 2016126465 A1 | 8/2016 |
| WO | 2016172106 A1 | 10/2016 |

* cited by examiner

IMPLANTABLE MEDICAL DEVICE FOR VASCULAR DEPLOYMENT

CROSS REFERENCE TO RELATED APPLICATIONS

This application claims the benefit of provisional U.S. Patent Application No. 62/609,565, filed Dec. 22, 2017, which is hereby incorporated by reference in its entirety.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

SUMMARY

This disclosure provides design, delivery and deployment methods, and clinical usage alternatives for medical devices. In one example, the disclosure is directed to implantable medical devices that may be configured to be disposed within the vasculature near a patient's heart in order to pace a portion of the patient's heart and/or to sense electrical activity within the patient's heart. In some cases, an implantable medical device may be implantable within the vasculature near the right atrium of the patient's heart, and may be configured to pace the right atrium of the patient's heart and/or sense cardiac signals in the right atrium of the patient's heart.

In a first example, a leadless cardiac device may be configured for deployment within a patient's vasculature at a location near the patient's heart. The leadless cardiac device may comprise a housing configured to be positioned within the patient's vasculature proximate the patient's heart, the elongated housing having a proximal end and a distal end, a power source disposed within the elongated housing, circuitry disposed within the elongated housing and operatively coupled to the power source, the circuitry configured to pace the patient's heart and/or sense electrical activity of the patient's heart, a first electrode fixed relative to the elongated housing and operatively coupled to the circuitry, a second electrode fixed relative to the elongated housing and operatively coupled to the circuitry, the second electrode spaced from the first electrode and positioned along a side wall of the elongated housing, a distal extension extending distally from the distal end of the elongated housing, the distal extension defining a lumen extending from a side port proximate a proximal end of the distal extension to a distal opening proximate a distal end of the distal extension and including a distal electrode positioned at distal end thereof and operatively coupled to the circuitry and configured to provide pacing pulses to the Bundle of His, and an expandable anchoring mechanism releasably coupled to the elongated housing, the expandable anchoring mechanism having a collapsed configuration for delivery and an expanded configuration that locates the leadless cardiac device within the patient's vasculature.

Alternatively or additionally to any of the examples above, in another example, the distal electrode may be slidably and rotatably disposed within the lumen of the distal extension.

Alternatively or additionally to any of the examples above, in another example, the leadless cardiac device may further comprise an actuation mechanism disposed within the lumen of the distal extension and coupled to the distal electrode.

Alternatively or additionally to any of the examples above, in another example, the actuation mechanism may be configured to direct the distal electrode toward a side wall of the patient's vasculature.

Alternatively or additionally to any of the examples above, in another example, the distal electrode may comprise a helical electrode.

Alternatively or additionally to any of the examples above, in another example, the helical electrode may be configured to be fixated to the Bundle of His.

Alternatively or additionally to any of the examples above, in another example, the distal electrode may comprise a curved tine electrode.

Alternatively or additionally to any of the examples above, in another example, the curved tine electrode may be configured to be fixated to the Bundle of His.

Alternatively or additionally to any of the examples above, in another example, the distal extension may increase in flexibility from the proximal end to the distal end.

Alternatively or additionally to any of the examples above, in another example, the leadless cardiac device may further comprise one or more intermediate electrodes positioned on the distal extension at a location proximal to the distal electrode.

Alternatively or additionally to any of the examples above, in another example, the expandable anchoring mechanism may be configured to bring at least one of the first or second electrodes of the housing in contact with a vessel wall.

Alternatively or additionally to any of the examples above, in another example, the expandable anchoring mechanism may be configured to anchor the leadless cardiac device in the patient's superior vena cava proximate the patient's right atrium.

Alternatively or additionally to any of the examples above, in another example, the expandable anchoring mechanism may be configured to anchor the leadless cardiac device in the patient's inferior vena cava proximate the patient's right atrium.

Alternatively or additionally to any of the examples above, in another example, the distal extension may be configured to extend into the right atrium.

Alternatively or additionally to any of the examples above, in another example, the one or more intermediate electrodes may be configured to sense atrial events.

In another example, a leadless cardiac device may be configured for deployment within a patient's vasculature at a location near the patient's heart. The leadless cardiac device may comprise a housing configured to be positioned within the patient's vasculature proximate the patient's heart, the elongated housing having a proximal end and a distal end, a power source disposed within the elongated housing, circuitry disposed within the elongated housing and operatively coupled to the power source, the circuitry configured to pace the patient's heart and/or sense electrical activity of the patient's heart, a first electrode fixed relative to the elongated housing and operatively coupled to the circuitry, a second electrode fixed relative to the elongated housing and operatively coupled to the circuitry, the second electrode spaced from the first electrode and positioned along a side wall of the elongated housing, a distal extension extending distally from the distal end of the elongated housing, the distal extension defining a lumen extending from a side port proximate a proximal end of the distal extension to a distal opening proximate a distal end of the distal extension and including a distal electrode positioned at distal end thereof and operatively coupled to the circuitry and configured to provide pacing pulses to the Bundle of His, and an expandable anchoring mechanism releasably coupled to the elongated housing, the expandable anchoring mechanism having a collapsed configuration for delivery and an expanded configuration that locates the leadless cardiac device within the patient's vasculature.

Alternatively or additionally to any of the examples above, in another example, the distal electrode may be slidably and rotatably disposed within the lumen of the distal extension.

Alternatively or additionally to any of the examples above, in another example, the leadless cardiac device may further comprise an actuation mechanism disposed within the lumen of the distal extension and coupled to the distal electrode.

Alternatively or additionally to any of the examples above, in another example, the actuation mechanism may be configured to direct the distal electrode toward a side wall of the patient's vasculature.

Alternatively or additionally to any of the examples above, in another example, the distal electrode may comprise a helical electrode.

Alternatively or additionally to any of the examples above, in another example, the helical electrode may be configured to be in contact with the Bundle of His.

Alternatively or additionally to any of the examples above, in another example, the distal electrode may comprise a curved tine electrode.

Alternatively or additionally to any of the examples above, in another example, the curved tine electrode may be configured to be in contact with the Bundle of His.

Alternatively or additionally to any of the examples above, in another example, the distal extension may increase in flexibility from the proximal end to the distal end.

Alternatively or additionally to any of the examples above, in another example, the leadless cardiac device may further comprise one or more intermediate electrodes positioned on the distal extension at a location proximal to the distal electrode.

Alternatively or additionally to any of the examples above, in another example, the expandable anchoring mechanism may be configured to bring at least one of the first or second electrodes of the housing in contact with a vessel wall.

Alternatively or additionally to any of the examples above, in another example, the expandable anchoring mechanism may be configured to anchor the leadless cardiac device in the patient's superior vena cava proximate the patient's right atrium.

Alternatively or additionally to any of the examples above, in another example, the expandable anchoring mechanism may be configured to anchor the leadless cardiac device in the patient's inferior vena cava proximate the patient's right atrium.

Alternatively or additionally to any of the examples above, in another example, the distal extension may be configured to extend into the right atrium.

Alternatively or additionally to any of the examples above, in another example, the one or more intermediate electrodes may be configured to sense atrial events.

In another example, a leadless cardiac device may be configured for deployment within a patient's vasculature at a location near the patient's heart. The leadless cardiac device may comprise a housing configured to be positioned within the patient's vena cava proximate the patient's right atrium, the elongated housing having a proximal end and a distal end, a power source disposed within the elongated housing, circuitry disposed within the elongated housing and operatively coupled to the power source, the circuitry configured to pace the patient's heart and/or sense electrical activity of the patient's heart, a first electrode fixed relative to the elongated housing and operatively coupled to the circuitry, a second electrode fixed relative to the elongated housing and operatively coupled to the circuitry, the second electrode spaced from the first electrode and positioned along a side wall of the elongated housing, an expandable anchoring mechanism releasably coupled to the elongated housing, the expandable anchoring mechanism having a collapsed configuration for delivery and an expanded configuration that locates the leadless cardiac device within the patient's vasculature, and a distal extension extending distally from the distal end of the elongated housing. The distal extension may comprise a lumen extending from a side port proximate a proximal end of the distal extension to a distal opening proximate a distal end of the distal extension, a distal electrode positioned at distal end thereof and operatively coupled to the circuitry and configured to provide pacing pulses to the Bundle of His, and an actuation mechanism slidably and rotatably disposed within the lumen of the distal extension and mechanically coupled to the distal electrode, wherein the actuation mechanism has a curved end configured to direct the distal ends way from a longitudinal axis of the distal extension when the actuation mechanism is distally actuated.

Alternatively or additionally to any of the examples above, in another example, the distal electrode may comprise a helical electrode.

Alternatively or additionally to any of the examples above, in another example, the distal electrode may comprise a curved tine electrode.

Alternatively or additionally to any of the examples above, in another example, the expandable anchoring device may be configured to position a side wall of the elongated housing in contact with a vessel wall.

In another example, a leadless cardiac device may be configured for deployment within a patient's vasculature at a location near the patient's heart. The leadless cardiac device may comprise a housing configured to be positioned within the patient's vena cava proximate the patient's right atrium, the elongated housing having a proximal end and a distal end, a power source disposed within the elongated housing, circuitry disposed within the elongated housing and operatively coupled to the power source, the circuitry configured to pace the patient's heart and/or sense electrical activity of the patient's heart, a first electrode fixed relative to the elongated housing and operatively coupled to the circuitry, a second electrode fixed relative to the elongated housing and operatively coupled to the circuitry, the second electrode spaced from the first electrode and positioned along a side wall of the elongated housing, an expandable anchoring mechanism releasably coupled to the elongated housing, the expandable anchoring mechanism having a collapsed configuration for delivery and an expanded configuration that locates the leadless cardiac device within the patient's vasculature, and a distal extension extending distally from the distal end of the elongated housing and configured to be positioned in the right atrium. The distal extension may comprise a lumen extending from a side port proximate a proximal end of the distal extension to a distal opening proximate a distal end of the distal extension, a distal helical electrode positioned at distal end thereof and operatively coupled to the circuitry and configured to provide pacing pulses to the Bundle of His, an intermediate bipolar electrode pair positioned proximal to the distal electrode and configured to sense atrial activity, and an actuation mechanism slidably and rotatably disposed within the lumen of the distal extension and mechanically coupled to the distal electrode, wherein the actuation mechanism has a curved end configured to direct the distal electrode away from a longitudinal axis of the distal extension when the actuation mechanism is distally actuated and rotational actuation is configured to twist the distal helical electrode into adjacent tissue.

The above summary of some illustrative embodiments is not intended to describe each disclosed embodiment or every implementation of the present disclosure. The Figures and Description which follow more particularly exemplify these and other illustrative embodiments.

BRIEF DESCRIPTION OF THE FIGURES

The disclosure may be more completely understood in consideration of the following description in connection with the accompanying drawings, in which.

Figure 1:
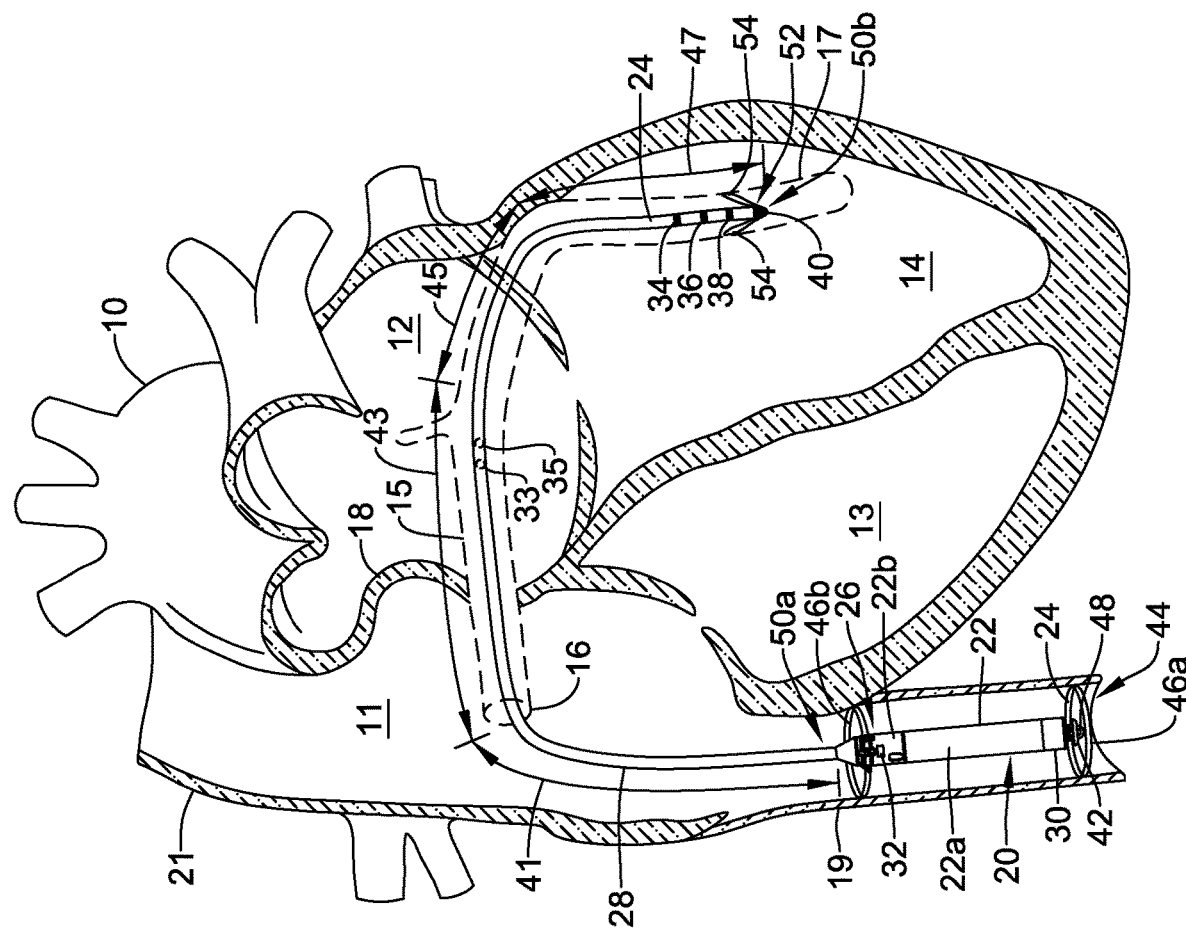
FIG. 1 is a schematic diagram of an example leadless pacing device implanted within a heart.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g., a battery), and associated electrical circuitry for controlling the pacing/sensing electrodes, and thus provide electrical stimulation to heart tissue and/or sense a physiological condition. In some cases, the leadless cardiac pacemakers may include a proximal and/or a distal extension extending from the small capsule, where the extension(s) may include one or more pacing/sensing electrodes. The capsule may be delivered to the heart using a delivery device which may be advanced through a femoral vein, into the inferior vena cava, into the right atrium, through the tricuspid valve, and into the right ventricle. Alternatively, the capsule may be delivered through a superior approach accessed through the subclavian vein or the internal jugular vein. In some cases, it may be desirable to provide alternative modular leadless pacing systems and implantation locations.

The leadless pacing device described herein may detect and treat cardiac arrhythmias, and more particularly, deliver electrical stimulation therapy to a right atrium, left atrium, right atrium, and/or a left ventricle of a heart of a patient. For instance, one or more devices may be implanted on or within a patient's heart, and the one or more devices may be configured to deliver electrical stimulation therapy to one or more chambers of the patient's heart in accordance with one or more therapy programs and/or to treat one or more types of detected cardiac arrhythmias. Some example electrical stimulation therapies include bradycardia therapy, cardiac resynchronization therapy (CRT), anti-tachycardia pacing (ATP) therapy, defibrillation and/or cardioversion therapy, and the like. Some example cardiac arrhythmias include atrial fibrillation or atrial flutter, ventricular fibrillation, and tachycardia. The leadless pacing device may also be configured to operate in cooperation with another medical pacing device, such as, but not limited to a leadless pacing device positioned within the left ventricle and/or a subcutaneous implantable cardioverter-defibrillator (S-ICD).

FIG. 1 is a conceptual diagram of an illustrative system for delivering electrical stimulation therapy to a patient's heart, including delivering electrical stimulation therapy to a right atrium, left atrium, right atrium, and/or a left ventricle of the patient's heart. FIG. 1 shows an illustrative leadless pacing device 20 implanted in and around heart 10. Heart 10 of FIG. 1 is depicted showing a right atrium 11, a left atrium 12, a right ventricle 13, a left ventricle 14, a coronary sinus 15, a coronary sinus ostium 16, a great cardiac vein 17, a septum 18, and a superior vena cava (SVC) 21. In the illustrative example, the leadless pacing device is illustrated as positioned within the inferior vena cava 19. However, the leadless pacing device 20 can be positioned in other regions in and around the heart 10. For example, the leadless pacing device 20 may be positioned in the coronary sinus 15, the SVC 21, the atria 11,12, the ventricles 13, 14, or other surrounding vasculature, as desired.

In the example of FIG. 1, the leadless pacing device 20 includes a housing 22 having a proximal end 24 and a distal end 26 and a distal extension 28 extending distally of the distal end 26 of the housing 22. However, in some instances, the distal extension 28 may not be included and/or one or more other distal and/or proximal extensions may be included. The housing 22 may be a single portion or may have a first portion 22a (e.g., a can or body), a second portion 22b (e.g., a head or molded portion), and/or one or more other portions. It is contemplated that the housing 22 need not have the same cross sectional shape along its entire length. When implanted, the housing 22 may be fully or partially disposed within the IVC 19 or SVC 21 of the patient's heart 10, while the distal extension 28 may be fully or partially disposed within a vessel extending from the heart 10 and/or IVC 19/SVC 21 and/or a chamber of the heart 10 such as, but not limited to the coronary sinus 15, the great cardiac vein 17, an anterior interventricular vein, and/or other laterally descending vessel, the right atrium 11, and/or the right ventricle 13.

The housing 22 may have any dimension suitable for implantation at a target location within the heart 10 of a patient. In one example, the housing 22 may have a cross-section diameter or area sufficient to fit within the IVC 19, SVC 21, and/or coronary sinus 15. The IVC 19 and SVC 21 may have a larger cross-sectional diameter than the coronary sinus 15. For example, the IVC may have a normal diameter in the range of 12-20 millimeters (mm), the SVC 21 may have a normal diameter in the range of 15-22 mm, and the coronary sinus may have a normal diameter in the range of 4-12 mm. As such, the IVC 19 or SVC 21 may accommodate a larger housing than the coronary sinus 15. The size of the housing 22 may be selected to maximize the internal space for control circuitry and batteries while still allowing for sufficient blood flow through the vasculature.

The housing 22 may have one or more textures on an exterior surface thereof. In some cases, the texture(s) of the housing 22 may include a first texture that facilitates stabilization of the housing 22 at a location within the patient and a second texture that facilitates blood passing by the housing 22. In one example of when the housing 22 may be configured for placement within the IVC 19 or SVC 21 of a patient, a first side (e. of the housing 22 intended to be adjacent to and/or touching excitable myocardial tissue may have a texturized surface (e.g., with a rough texture) to facilitate stabilizing the housing 22 at an intended location and a second side may have a smooth surface relative to the texturized first side of the housing 22 to facilitate blood and/or other fluids passing the housing 22 within the coronary sinus 15. The texturized surface may be texturized through sandblasting, beadblasting, sodium bicarbonate-blasting, electropolishing, depositing, and/or one or more other texturizing techniques. The smooth surface may be smooth from polishing, applying a protective layer or coating, and/or one or more other smoothing techniques.

In some embodiments, the leadless pacing device 20 may additionally include one or more electrodes. In one example, the housing 22 may support a first electrode 30 and a second electrode 32, while the distal extension 28 may support a distal electrode. In some cases, the distal electrode may include a plurality of electrodes (e.g., a first proximal ring electrode 34, a second proximal ring electrode 36, a third proximal ring electrode 38, a distal ring electrode 40, and/or one or more other electrodes). Although the electrodes described may be indicated as being ring electrodes, other electrode types may be utilized depending on the application. In some cases, the distal extension 28 may include electrodes 33, 35 positioned at a location between the proximal 50a and distal ends 50b thereof.

The distal extension 28 may include a plurality of conductors (not explicitly shown) configured to electrically couple the electrodes 34-40 to the power source and control circuitry disposed within the housing 22. The conductors may be coated or covered by an insulating polymeric coating or tubing. It is contemplated that the distal extension 28 may vary in flexibility from the proximal end 50a to the distal end 50b thereof. For example, the distal extension 28 may have a first flexibility near the proximal end 50a and another flexibility near the distal end 50b. In some cases, the distal end 50b may be more flexible than the proximal end 50a. In some examples, the flexibility may be varied by forming sections 41, 43, 45, 47 of the distal extension with a series of different durometers where the sections 41, 43, 45, 47 become progressively more flexible. In other words, the distal extension may have a discrete or step-wise transition in flexibility at each section 41, 43, 45, 47. It is further contemplated that a step-wise transition in flexibility may also be achieve by changing the wall thickness of the polymer coating or tubing at each section 41, 43, 45, 47. While four discrete sections 41, 43, 45, 47 are described, it is contemplated that the distal extension 28 may include any number of sections having any combination of flexibilities or hardness (durometer properties), such as, but not limited to one, two, three, four, or more. In another example, the distal extension 28 may have a flexibility which continuously varies over the length of the extension. In some cases, this may be accomplished by having a polymer coating thickness which continuously changes (e.g., becomes progressively thinner from the proximal end 50a to the distal end 50b in a tapered manner). In yet another example, the conductors within the lead extension 28 could be formed of a material having a varying stiffness. In another example, a separate non-conducting element (such as a nitinol wire) may be provided without the lead extension 28 to provide graduated levels of stiffness or flexibility along the length of the distal extension 28. It is contemplated that varying the stiffness of the distal extension 28 may provide stiffness support to help delivery (e.g., increase pushability while allowing the distal most portion to navigate tortuous vasculature). It is further contemplated that varying the stiffness of the distal extension 28 may also help prevent dislodgment.

Although electrodes 30, 32 supported by the housing 22 are depicted as disposed on both of the first portion 22a and the second portion 22b of the housing 22, respectively, in some cases, the number and location of electrodes disposed on housing 22 may vary, depending on the application. For example, the leadless pacing device 20 may have electrodes disposed only on one of the first housing portion 22a or the second housing portion 22b, where the leadless pacing device 20 includes two housing portions. It may be desirable to arrange electrodes on the housing 22 at various longitudinal lengths of the housing 22 to facilitate creating good contact between an electrode and a wall of the IVC 19, if so positioned. In some instances, the leadless pacing device 20 may not have any electrodes disposed on the housing 22.

In one example arrangement of the electrodes 30, 32 on the housing 22, the first electrode 30 that is located on the first portion 22a of the housing 22 may be an anode electrode and the second electrode 32 that is located on the second portion 22b of the housing 22 may be a cathode electrode. However, as the electrodes may be bipolar electrodes, the first electrode 30 in the example arrangement may be changed to a cathode electrode and the second electrode 32 in the example arrangement may be changed to an anode electrode. The polarity of paired bipolar electrodes may be switched regardless of locations of the electrodes.

When provided, the electrodes of the leadless pacing device 20 may be used to deliver electrical stimulation to heart 10, and/or sense one or more physiologic signals. In some cases, the leadless pacing device 20 may use one or more of the electrodes (e.g., electrodes 30-40 or other electrodes) to communicate with one or more other devices, such as, but not limited to, one or more other leadless cardiac pacemakers and/or an implantable cardioverter defibrillator. In some instances, the leadless pacing device 20 may communicate using conducted communication techniques and may deliver and/or receive communication signals through one or more of the electrodes (e.g., the electrodes 30-40 or other electrodes).

In some instances, the housing 22 may include a proximal member 42 (e.g., a docking hub or other member) which extends generally from the proximal end of the housing 22. In the example shown in FIG. 1, the proximal member 42 may extend from the first portion 22a of the housing 22. During implantation, the proximal member 42 may be releasably coupled to a positioning device (not shown in FIG. 1). When coupled, movement of the positioning device may translate to the housing 22, thereby allowing a user, such as a physician, to maneuver the housing 22 into a proper position within the heart 10, for example into or proximate the IVC 19. Alternatively, or additionally, the proximal member 42 may be configured to facilitate retrieval of the leadless pacing device 20.

The leadless pacing device 20 include an expandable anchoring mechanism 44. The expandable anchoring mechanism 44 may, for example, have a collapsed or delivery configuration to facilitate delivery through the vasculature to a location such as but not limited to, the SVC or the IVC. The expandable anchoring mechanism 44 may also have an expanded configuration that locates the leadless pacing device 20 within the vasculature and secures the leadless pacing device 20 in place, with the electrode 30, 32 in engagement with the vasculature wall, although this is not required. In some embodiments, the expandable anchoring mechanism may be configured to position the leadless pacing device 20 such that the housing 22 is not in contact with a vessel wall. In some cases, the expandable anchoring mechanism 44 may be configured to anchor the leadless pacing device 20 in the vasculature such that the longitudinal axis of the housing 22 is positioned parallel or substantially parallel (within 20 degrees of parallel) with blood flow through the vasculature. In the embodiment illustrated in FIG. 1, the expandable anchoring mechanism 44 may include a proximal fixation elements 46a and a distal fixation element 46b (collectively, 46) and will be described in more detail with respect to FIGS. 2A and 2B. In some cases, the expandable anchoring mechanism 44 may resemble or be a stent, such as a braided stent, a woven stent or a laser cut stent. The expandable anchoring mechanism 44 may be self-expanding or could be balloon-expandable. It is contemplated that the expandable anchoring mechanism 44 may be formed of any desired metallic or polymeric material, as desired. Some illustrative expandable anchoring mechanisms are described in commonly assigned patent application Ser. No. 15/590,811, entitled IMPLANTABLE MEDICAL DEVICE FOR VASCULAR DEPLOYMENT and filed on May 9, 2017, which is hereby incorporated by reference.

In some instances, the leadless pacing device 20 may be delivered from a guide catheter (not shown in FIG. 1), and the portion of the guide catheter surrounding the housing 22 may conform to the housing 22 to create a secure connection between the guide catheter and the housing 22. It is further contemplated that the guide catheter may be configured to maintain the expandable anchoring mechanism 44 in a collapsed configuration during delivery. When in position, the guide catheter may be retracted, or a stylet or other pushing device may push the housing 22 out of the guide catheter. In these cases, the proximal member 42 may further include a tether anchor 48. During delivery, a tether may be coupled to the tether anchor 48 to allow a user to pull the housing 22 back within the guide catheter for further positioning. In some instances, the tether may be a string, and the string may be coupled to the tether anchor 48 by looping around the tether anchor 48. To release the tether from housing 22, a user may simply cut the tether or pull one end of the tether until the tether unloops itself from the tether anchor 48.

Although the distal extension 28 is depicted in FIG. 1, in some instances, the leadless pacing device 20 may not include the distal extension 28. Where the leadless pacing device 20 includes the distal extension 28 extending from the distal end of the housing 22 (e.g., the second portion 22b of the housing 22, as shown in FIG. 1). When included, the distal extension 28 may extend into the coronary sinus 15 and be secured within coronary sinus 15. In some cases, the distal extension 28 may extend through the coronary sinus 15 and into the great cardiac vein 17, or one or more other vessels extending from the coronary sinus. In other cases, the distal extension 28 may be positioned with the right atrium or right ventricle.

The distal extension 28 may include a proximal end 50a and a distal end 50b. The distal end 50b of the distal extension 28 may include one or more fixing members 52. The fixing members 52 may help secure the distal end 24b of the distal extension 28 within coronary sinus 15 or great cardiac vein 17. The fixing members 52 may include one or more anchors 54 (e.g., tines, helical coils, talons, or other anchors) made of silicon, a biocompatible polymer, a biocompatible metal, another biocompatible material, a shape memory material (e.g., nitinol or other shape memory material), and/or a bioabsorbable. A bioabsorbable material may be utilized to facilitate removal of the leadless pacing device 20 from a patient as endothelial growth may otherwise occur over the anchors 54. The anchors 54 may extend radially outward from the distal extension 28 and press against the walls of coronary sinus 15. The force between the anchors 54 and the walls of coronary sinus 15 may hold the distal end 50b of the distal extension 28 in place.

The anchors 54 of the fixing member 52 (e.g., and thus the fixing member 52) may be angled to allow easy insertion through body vessels (e.g., veins, coronary sinus, etc.), while facilitating fixation against valves of body vessels at target sites and/or implant locations. In some cases, the anchors 54 of the fixing members 52 may be angled proximally so as to facilitate distal insertion into and/or through body vessels and may extend radially outward from a longitudinal axis of the distal extension 28 in the proximal direction to engage a valve in the body vessel and fixate the distal extension 28 at an implant location (e.g., to prevent or limit proximal movement).

Although one fixing member 52 is depicted on the distal extension 28 in the Figures, the distal extension 28 may support one or more additional fixing members that are axially spaced from the fixing member 52 depicted in the Figures. In other instances, the distal extension 28 may not include a fixing member 52. Alternatively, the fixing member 52 may be positioned such that it extends longitudinally from the distal end 50b of the distal extension 28. In such a configuration, the fixing member 52 may be configured to engage tissue adjacent to (or generally orthogonal to the longitudinal axis of the distal extension 28) the distal end 50b such as, but not limited to, a heart wall.

In some cases, the fixing member 52 may include one or more electrodes or wire loops and may act as an antenna to communicate with and/or receive electrical energy from one or more other devices. For example, the leadless pacing device 20 may receive an energy transfer and/or communicate using inductive and/or conductive communication techniques through electrodes and/or wire loops of the fixing member 52.

As mentioned above, the distal extension 28 may include one or more electrodes (e.g., electrodes 34-40). In some of these instances, some of the electrodes 34, 36, 38, 40 may be disposed proximate the distal end 50b of the distal extension 28 and away from the housing 22, however in other instances, one or more of the electrodes on the distal extension 28 may span a length (e.g., an entire length) of the distal extension 28.

In some cases, the electrodes on the distal extension 28 may be used to deliver electrical stimulation to the heart 10. For example, the leadless pacing device 20 may deliver electrical stimulation to the left ventricle 14 of heart 10 through a set of one or more of electrodes (e.g., a set from the electrodes 34, 36, 38, 40 or other electrodes). It is contemplated that the chamber of the heart receiving the electrical stimulation may be selected through selective placement of the distal end 50b of the distal extension 28. In some cases, the leadless pacing device 20 may deliver electrical stimulation to the left ventricle 14 of heart 10 using two or more of the electrodes 34-40 either simultaneously or with a delay (e.g. via multi-electrode pacing). In some additional or alternative cases, the leadless pacing device 20 may use one or more of the electrodes 34-40 to communicate with one or more other devices (e.g., the electrodes 34-40 may act as an antenna). For example, the leadless pacing device 20 may receive an energy transfer and/or communicate using inductive or conductive communication techniques through one or more of the electrodes 34-40.

The electrodes 30-40 and/or other electrodes on the leadless pacing device 20 may be able to sense electrical signals, provide electrical stimulation signals, or sense electrical signals and provide electrical stimulation signals. Signal processing, communication, and/or therapy pulse generation may take place at any portion of the leadless pacing device where the appropriate processing modules may be located. In one example, signal processing, communication, and therapy pulse generation for the electrodes (e.g., electrodes 30-40 and/or other electrodes) of the leadless pacing device 20 may take place in modules within or supported by the housing 22, but this is not required.

The electrodes 30-40 and/or other electrodes of the leadless pacing device 20 may be configured to perform near-field and/or far-field sensing of cardiac activation events. "Near-field" sensing of cardiac activation events refers to sensing cardiac activation events that originate in a local chamber where the corresponding electrode is located (e.g., the same chamber at which an electrode is sensing). "Far-field" sensing of cardiac activation events refers to sensing cardiac activation events that originate in a chamber other than the local chamber where the corresponding electrode is located. For example, if an electrode of the leadless pacing device 20 is located in the coronary sinus 15 with an electrode adjacent a wall of the coronary sinus 15 that forms a wall of the right atrium 11, the electrode is near-field sensing right atrium activation events and is far-field sensing left atrium activation events, left, ventricle activation events, and right ventricle activation events.

In the example of FIG. 1 where the leadless pacing device 20 is implanted in the IVC 19 and a vessel (e.g., the great cardiac vein 17) extending from the coronary sinus 15, the first electrode 30 (e.g., a proximally located electrode on the housing 22) may be located in the IVC 19 adjacent the right ventricle 13, the second electrode 32 (e.g., a distally located electrode on the housing 22) may be located in the IVC 19 adjacent the right atrium 11, and the electrodes 34-40 supported by the distal extension 28 may be located in may be located in the great cardiac vein 17 adjacent the left ventricle 14. In such an implanted configuration, the first electrode 30 may sense near-field signals of atrial activation events (P-waves) in and provide pacing pulses to cardiac tissue of the right atrium 11, the second electrode may sense near-field signals of atrial activation events (P-waves) in and provide pacing pulses to cardiac tissue of the left atrium 12, and the electrodes 34, 36, 38, 40 supported by the distal extension 28 may sense near-field signals of ventricular activation events (R-waves) originating from atria and conducted through the atrioventricular node and His-Purkinje path in and provide pacing pulses to cardiac tissue of the left ventricle 14.

Additionally or alternatively, the electrodes 30-40 or other electrodes of the leadless pacing device 20 may sense signals through far-field sensing. For example, the electrodes 30, 32 that may be supported by the housing 22 may sense far-field ventricular activation activity (R-waves) and the electrodes 34-40 supported by the distal extension 28 may sense far-field atrial activation activity (P-waves). However, such sensed signals may be attenuated and delayed and/or the amplitude and duration may be insufficient for reliable sensing of atrial and ventricular activation activity and it may be necessary to consider signals sensed through near-field sensing when considering signals sensed through far-field sensing.

It is contemplated that there may be a number of different vectors between the electrodes 34-40 positioned on the distal extension 28 and the electrodes 30, 32 positioned on the housing 22. These vectors may be used to obtain various diagnostic and physiological parameters. For example, the vectors between electrodes 34-40 on the distal extension 28 and electrodes 30, 32 on the housing 22 may be used to monitor impedance correlated to fluid status (e.g., fluid surrounding the heart) and/or atrial or ventricular volumes. In another example, the vectors may be used to monitor respiration. It is further contemplated that the vectors may be used to optimize the ventricular pacing pulse. For example, the electrodes could be used to sense the right ventricle R-wave and time the left ventricle pacing pulse (e.g., negative or positive offset) according to the various levels of the R-wave fusion.

In some cases, the leadless pacing device 20 may be implanted as a single device (e.g. without one or more other leadless pacing devices or one or more implantable cardioverter defibrillators), which may provide electrical stimulation to the right atrium 11, the left atrium 12, right ventricle 13 and/or the left ventricle 14, as desired. For example, the leadless pacing device 20 may be configured to deliver electrical stimulation in accordance with a therapy program to treat atrial fibrillation or atrial flutter. However, in other cases, the leadless pacing device 20 may be implanted with one or more other leadless pacing devices and/or one or more other implantable cardioverter defibrillators implanted at one or more various locations in and/or around the heart 10.

In one example of using the leadless pacing device 20, the leadless pacing device 20 may be part of a single or multiple device system for delivering cardiac resynchronization therapy (CRT) to heart 10. In these examples, the leadless pacing device 20 may sense cardiac electrical signals in one or both of right atrium 11 and left atrium 12. Once the leadless pacing device 20 senses cardiac electrical signals propagating through the right atrium 11 and/or left atrium 12, the leadless pacing device 20 may deliver a pacing pulse to the left ventricle 14 after a delay period (e.g., an AV delay). The length of the delay period may be determined or chosen such that the leadless pacing device 20 may deliver a pacing pulse to the left ventricle 14 as the propagating cardiac electrical signals reach the right ventricle 13 and cause the right ventricle 13 to contract. In this manner, the leadless pacing device 20 may operate to provide synchronous contractions of the right ventricle 13 and the left ventricle 14. In some additional instances, the leadless pacing device 20 may adjust the delay period based on a sensed heart rate. For example, when the leadless pacing device 20 senses an increased heart rate, the leadless pacing device 20 may shorten the length of the delay period. Conversely, when the leadless pacing device 20 senses a lowered heart rate, the leadless pacing device 20 may lengthen the delay period.

As discussed, the leadless pacing device 20 may deliver pacing pulses to the right atrium 11 and/or the left atrium 12 via the coronary sinus 15. In these embodiments, the leadless pacing device 20 may begin counting the delay period at the time of or just after the leadless pacing device 20 delivers a pacing pulse to the right atrium 11 and/or the left atrium 12. As with the previously described embodiments, this may cause synchronous contractions of the right ventricle 13 and the left ventricle 14. Where the leadless pacing device 20 is part of a system with an additional leadless pacing device within the right ventricle 13, the leadless pacing device 20 may communicate a trigger to the additional leadless pacing device after the leadless pacing device 20 delivers a pacing pulse to the right atrium 11 and/or the left atrium 12. After receiving the trigger, the additional leadless pacing device may deliver a pacing pulse to the right ventricle 13 after its own delay period. In at least some of the examples, the delay period of the additional leadless pacing device and the delay period of the leadless pacing device 20 may be in alignment such that both of the additional leadless pacing device and the leadless pacing device 20 deliver pacing pulses to the right ventricle 13 and the left ventricle 14 synchronously. However, in other embodiments, the delay period of the additional leadless pacing device and the delay period of the leadless pacing device 20 may be different, for instance if conduction through the right ventricle 13 and left ventricle 14 differ, in order to cause right ventricle 13 and left ventricle 14 to contract synchronously.

Figure 2A:
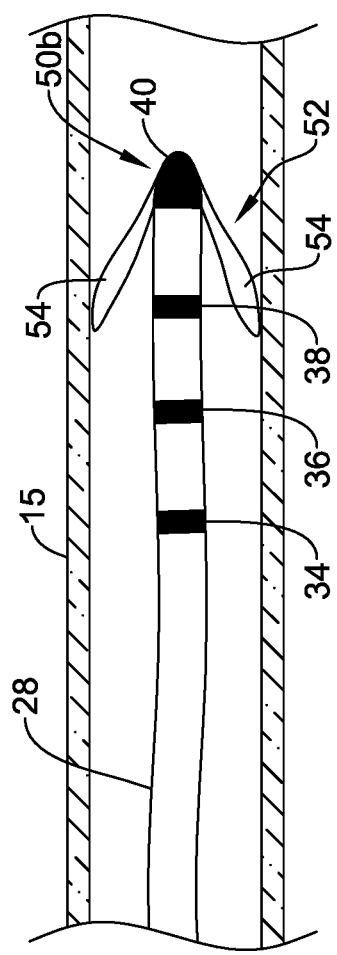
FIG. 2A is a schematic view of the leadless pacing device of FIG. 1 in an expanded configuration.
Figure 2A:
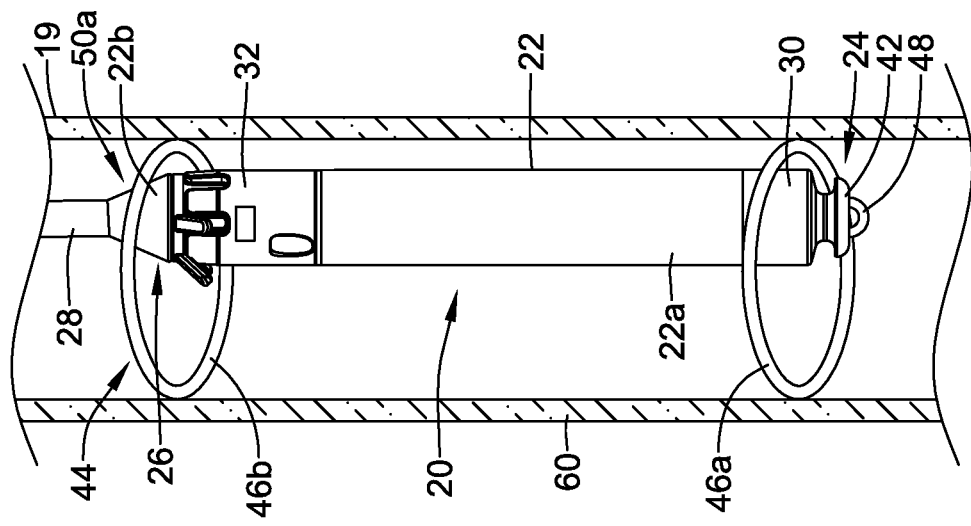

FIG. 2A illustrates a partial cross-sectional enlarged view of the leadless cardiac device 20 disposed within the IVC 19 and the distal extension 28 in the coronary sinus 15. In the illustrated embodiment, the expandable anchoring mechanism 44 is illustrated in the expanded configuration such that the proximal fixation element 46a and the distal fixation element 46b engage the vessel wall 60. In some cases, the housing 22 of the leadless cardiac device 20 may be configured to contact the vessel wall 60, as shown. However, it is contemplated that the expandable anchoring mechanism 44 may be configured to space the housing 22 of the leadless cardiac device 20 from the vessel wall 60. While the expandable anchoring mechanism 44 is illustrated as having two fixation elements 46, it is contemplated that the expandable anchoring mechanism 44 may include fewer than two or more than two fixation elements 46, as desired. In some cases, the proximal fixation element 46a may be secured to the housing 22 adjacent to the proximal member 42, although other locations may be suitable. The distal fixation element 46b may be secured to the housing 22 adjacent to the distal end 26 thereof, although other locations may be suitable.

The proximal fixation element 46a and the distal fixation element 46b may be formed from a ribbon-like element that is formed into a generally circular or oblong expanded shape. In other words, the proximal fixation element 46a and the distal fixation element 46b may be formed from an element having a cross-sectional shape in which the width dimension is greater than a thickness dimension. The proximal fixation element 46*a* and the distal fixation element 46*b* may be formed such that in the expanded configuration, the width dimension is configured to contact the vessel wall 60. It is contemplated that increasing the surface area of the proximal fixation element 46*a* and the distal fixation element 46*b* in contact with the vessel wall 60 may reduce the pressure exerted on the vessel wall 60. However, it is contemplated that the proximal fixation element 46*a* and the distal fixation element 46*b* may have any cross-sectional shape desired. Further, proximal fixation element 46*a* and the distal fixation element 46*b* need not have the same cross-sectional shape. It is further contemplated that the proximal fixation element 46*a* and/or the distal fixation element 46*b* may be formed from a plurality of braided or interwoven filaments configured to provide a robust structure configured to reduce fractures due to flexure fatigue. In some cases, the proximal fixation element 46*a* and/or the distal fixation element 46*b* may include a plurality of ring elements, as shown in FIGS. 3A and 3B. Further, while the fixation elements 46 are illustrated as having a generally round shape, it is contemplated that the fixation elements 46 may take other shapes as desired. In some cases, the fixation elements 46 may includes features that allow them to conform to differing size vessels, such as, but not limited to a sinusoidal shape.

In some cases, the expandable anchoring mechanism 44 may be formed from a shape memory material, such as, but not limited to, nitinol, such that the expandable anchoring mechanism 44 may be formed in an expanded configuration, biased into a collapsed configuration for delivery, and resume its preformed expanded configuration upon removal of the biasing force (e.g., without application of an external force). Alternatively, or additionally, the expandable anchoring mechanism 44 may be formed from a non-metallic material to minimize eddy currents for inductive powering or communication.

In some cases, the expandable anchoring mechanism 44 may be configured to perform more than one function. For example, in addition to fixating the leadless pacing device 20, the expandable anchoring mechanism 44 may also be configured to provide communication capabilities and/or measure physiological conditions. In some embodiments, the expandable anchoring mechanism 44 may include inductive charging and/or inductive communication windings. Alternatively, or additionally, the expandable anchoring mechanism 44 may include strain sensors configured to measure and/or transduce venous pressure. These are just examples. Other communication modalities and/or sensors may be included as desired.

Figure 2B:
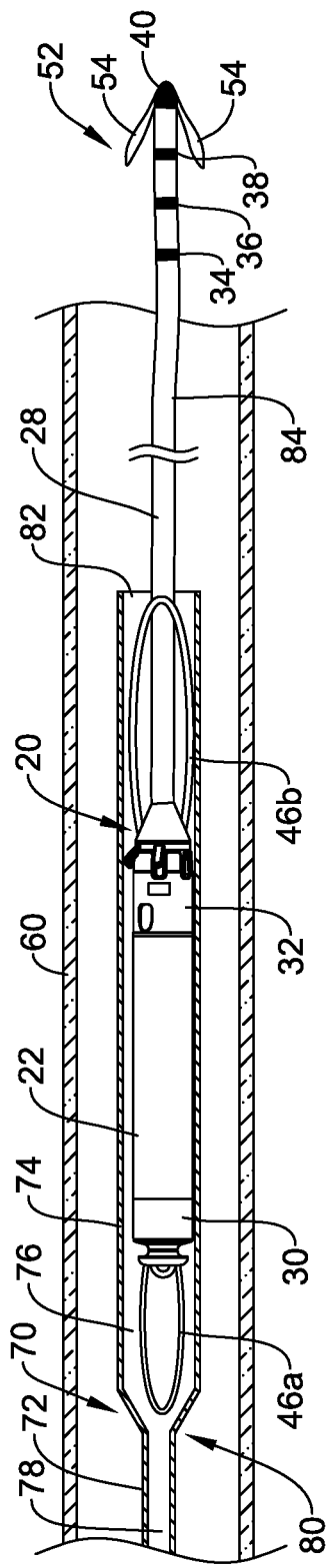
FIG. 2B is a schematic view of the leadless pacing device of FIG. 1 in an collapsed delivery configuration.

FIG. 2B illustrates a partial cross-sectional view of the illustrative leadless pacing device 20 of FIG. 2A disposed within a delivery system 70. The delivery system 70 may include an elongate tubular member 72 extending from a proximal end (not explicitly shown) configured to remain outside the body to a distal end portion 80. The elongate shaft 72 may include a lumen 78 extending from the proximal end to the distal end portion 80 thereof for slidably receiving another medical device such as, but not limited to a guidewire or a push/pull member. A distal holding section 74 may be attached to a distal end portion 80 of the elongate tubular member 72. The distal holding section 74 may be configured to receive the implantable device 20 therein. For example, the holding section 74 may define a cavity 76 in fluid communication with lumen 78 for slidably receiving the implantable device 20, and may include a distal opening 82 for slidable insertion and/or extraction of the implantable device 20 into and/or out of the cavity 76. In some cases, the distal extension 28 may include a lumen 84 extending entirely or partially therethrough. The lumen 84 may be configured to be advanced over guidewire and/or receive a stylet therein to facilitate positioning of the distal extension 28. While not explicitly shown, the distal extension 28 may include a side port adjacent the proximal end 50*a* thereof for receiving a guidewire or stylet into the lumen 84.

The distal holding section 74 may be configured to exert a biasing force on the expandable anchoring mechanism 44 to maintain the proximal fixation element 46*a* and the distal fixation element 46*b* in a collapsed configuration such that the leadless pacing device 20 has a reduced profiler for delivery. In some cases, the proximal fixation element 46*a* and the distal fixation element 46*b* may be collapsed such that they extend proximally and distally from the proximal and distal ends 24, 26 of the leadless pacing device 20, respectively. This may prevent the expandable anchoring mechanism 44 from overlapping the housing 22 during delivery which may minimize the delivery profile of the leadless pacing device 20.

In some cases, the delivery system 70 may include a plurality of elongated shafts (not explicitly shown) which may be operated in cooperation with one another to facilitate advancement of the delivery system through the vasculature and facilitate deployment of the leadless pacing device 20. For example, while not explicitly shown a push member or inner catheter may be disposed within the lumen 78 of the elongate shaft 72 to push and/or pull the leadless pacing device 20 to distally deploy and/or proximally retract the leadless pacing device 20, as desired. The push/pull member may be coupled to, or otherwise engage, the proximal member 42. For example, in some cases, the leadless pacing device 20 may be partially deployed and subsequently proximally retracted if repositioning of the leadless pacing device 20 is desired. It is contemplated that the distal fixation element 46*b* may be deployed and resheathed many times until the desired position is achieved. However, while the distal fixation element 46*b* may be resheathed, it may be more cumbersome. The expandable anchoring mechanism 44 may include radiopaque markers or a radiopaque material to facilitate positioning of the leadless pacing device 20 through the use of fluoroscopy and/or x-ray. In some cases, the proximal member 42 may be used to facilitate removal of the leadless pacing device 20, if so desired. It is contemplated that during removal of the leadless pacing device 20, the proximal fixation element 46*a* and the distal fixation element 46*b* may both collapse in a distal direction such that the proximal fixation element 46*a* is disposed over the housing 22 during removal. An illustrative delivery system for delivering a leadless cardiac device are described in commonly assigned patent application Ser. No. 14/919,310, entitled DELIVERY DEVICES AND METHODS FOR LEADLESS CARDIAC DEVICES and filed on Oct. 21, 2017, which is hereby incorporated by reference.

Figure 3:
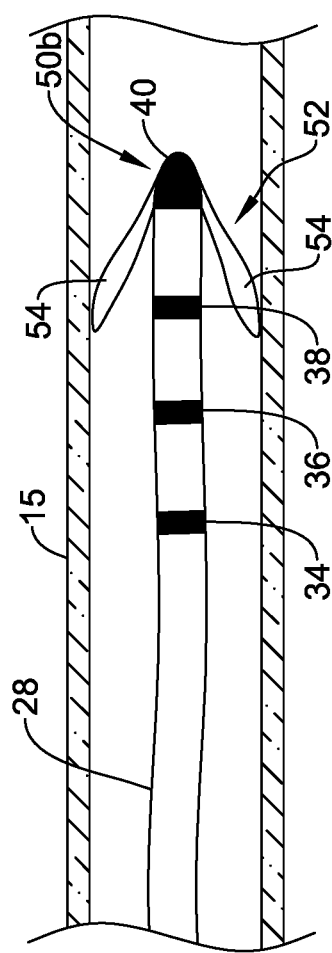
FIG. 3 is a schematic view of the leadless pacing device of FIG. 1 in an expanded configuration having an alternative anchoring mechanism.
Figure 3:
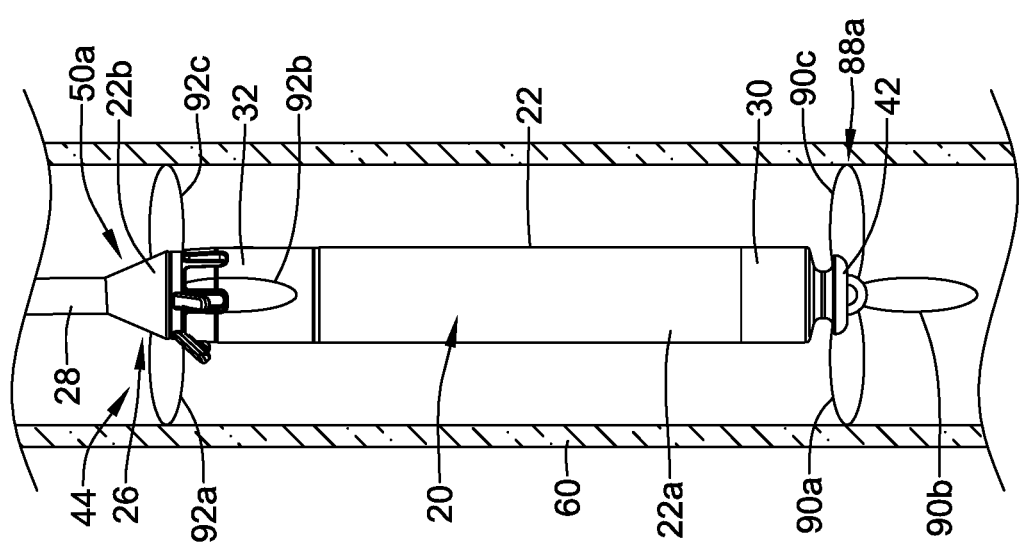

FIG. 3 illustrates another partial cross-sectional enlarged view of the leadless cardiac device 20 disposed within the IVC 19 and the distal extension 28 in the coronary sinus 15 having an alternative arrangement for the expandable anchoring mechanism 44. In the illustrated embodiment, the expandable anchoring mechanism 44 is illustrated in the expanded configuration such that the proximal fixation element 88*a* and the distal fixation element 88*b* (collectively, 88) engage the vessel wall 60. The expandable anchoring mechanism 44 may be configured to space the housing 22 of the leadless cardiac device 20 from the vessel wall 60, as shown. In some cases, positioning the leadless cardiac device 20 away from the vessel wall 60 may reduce or prevent fibrosis. However, the housing 22 may be biased against the vessel wall 60, as desired. While the expandable anchoring mechanism 44 is illustrated as having two fixation elements 88, it is contemplated that the expandable anchoring mechanism 44 may include fewer than two or more than two fixation elements 88, as desired.

The proximal fixation element 88*a* may be formed from a plurality of ring lobes 90*a*, 90*b*, 90*c* (collectively, 90). In some cases, the proximal fixation element 88*a* may be secured to the housing 22 adjacent to the proximal member 42, although other locations may be suitable. The distal fixation element 88*b* may be similarly formed from a plurality of ring lobes 92*a*, 92*b*, 92*c* (collectively 92). The distal fixation element 88*b* may be secured to the housing 22 adjacent to the distal end 26 thereof, although other locations may be suitable. While the proximal fixation element 88*a* and the distal fixation element 88*b* are illustrated as including the same number of lobes 90, 92, it is contemplated that they may have the same number or different number of lobes 90, 92 as desired. It is further contemplated that the proximal fixation element 88*a* and the distal fixation element 88*b* need not have the same structure. The lobes 90, 92 may be formed from a ribbon-like element (e.g., having a rectangular or oblong cross-section), a filament (e.g., having a circular cross-section, a plurality of interwoven or braided strands, or another other elongated structure desired. While not explicitly shown, the proximal fixation element 88*a* and the distal fixation element 88*b* may be collapsed into a reduced profile delivery configuration, as described with respect to FIGS. 2A and 2B. The expandable anchoring mechanism 44 may be configured to expand without the application of an external force after removal from the delivery device.

Figure 4:
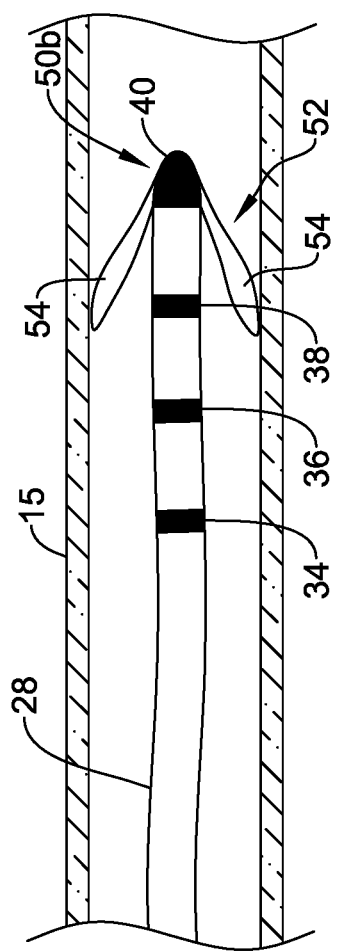
FIG. 4 is a schematic view of the leadless pacing device of FIG. 1 in an expanded configuration having another alternative anchoring mechanism.
Figure 4:
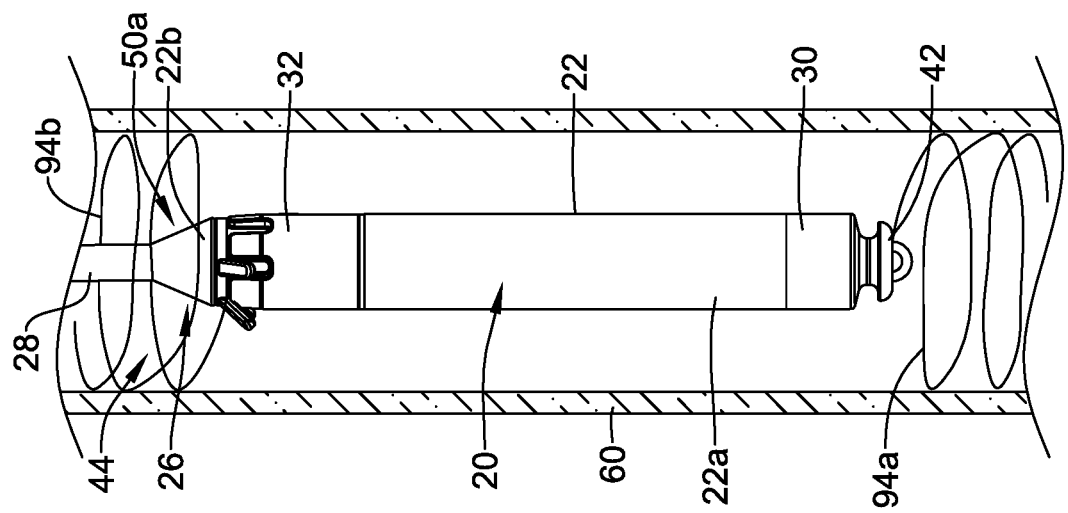

FIG. 4 illustrates another partial cross-sectional enlarged view of the leadless cardiac device 20 disposed within the IVC 19 and the distal extension 28 in the coronary sinus 15 having another alternative arrangement for the expandable anchoring mechanism 44. In the illustrated embodiment, the expandable anchoring mechanism 44 is illustrated in the expanded configuration such that the proximal fixation element 94*a* and the distal fixation element 94*b* (collectively, 94) engage the vessel wall 60. The expandable anchoring mechanism 44 may be configured to space the housing 22 of the leadless cardiac device 20 from the vessel wall 60, as shown. However, the expandable anchoring mechanism 44 may be configured to bias the housing 22 against the vessel wall 60, as desired. While the expandable anchoring mechanism 44 is illustrated as having two fixation elements 94, it is contemplated that the expandable anchoring mechanism 44 may include fewer than two or more than two fixation elements 94, as desired.

The proximal fixation element 94*a* may be formed from a helical element. In some cases, the proximal fixation element 94*a* may be secured to the housing 22 adjacent to the proximal member 42, although other locations may be suitable. The distal fixation element 94*b* may be similarly formed from a helical element. The distal fixation element 94*b* may be secured to the housing 22 adjacent to the distal end 26 thereof, although other locations may be suitable. It is contemplated that the characteristics of the helices may adjusted to achieve the desired positioning of the leadless cardiac device. In some cases, the curvature of the helix (for example, near the point of attachment to the device 20) may be adjusted to manipulate the position of the leadless cardiac device 20. While the proximal fixation element 94*a* and the distal fixation element 94*b* are illustrated as including a single helix, it is contemplated that they may have the same number or different number of fixation elements 94 as desired. It is further contemplated that the proximal fixation element 94*a* and the distal fixation element 94*b* need not have the same structure. The fixation elements 94 may be formed from a ribbon-like element (e.g., having a rectangular or oblong cross-section), a filament (e.g., having a circular cross-section, a plurality of interwoven or braided strands, or another other elongated structure desired. While not explicitly shown, the proximal fixation element 94*a* and the distal fixation element 94*b* may be collapsed into a reduced profile delivery configuration, as described with respect to FIGS. 2A and 2B. The expandable anchoring mechanism 44 may be configured to expand without the application of an external force after removal from the delivery device.

Figure 5A:
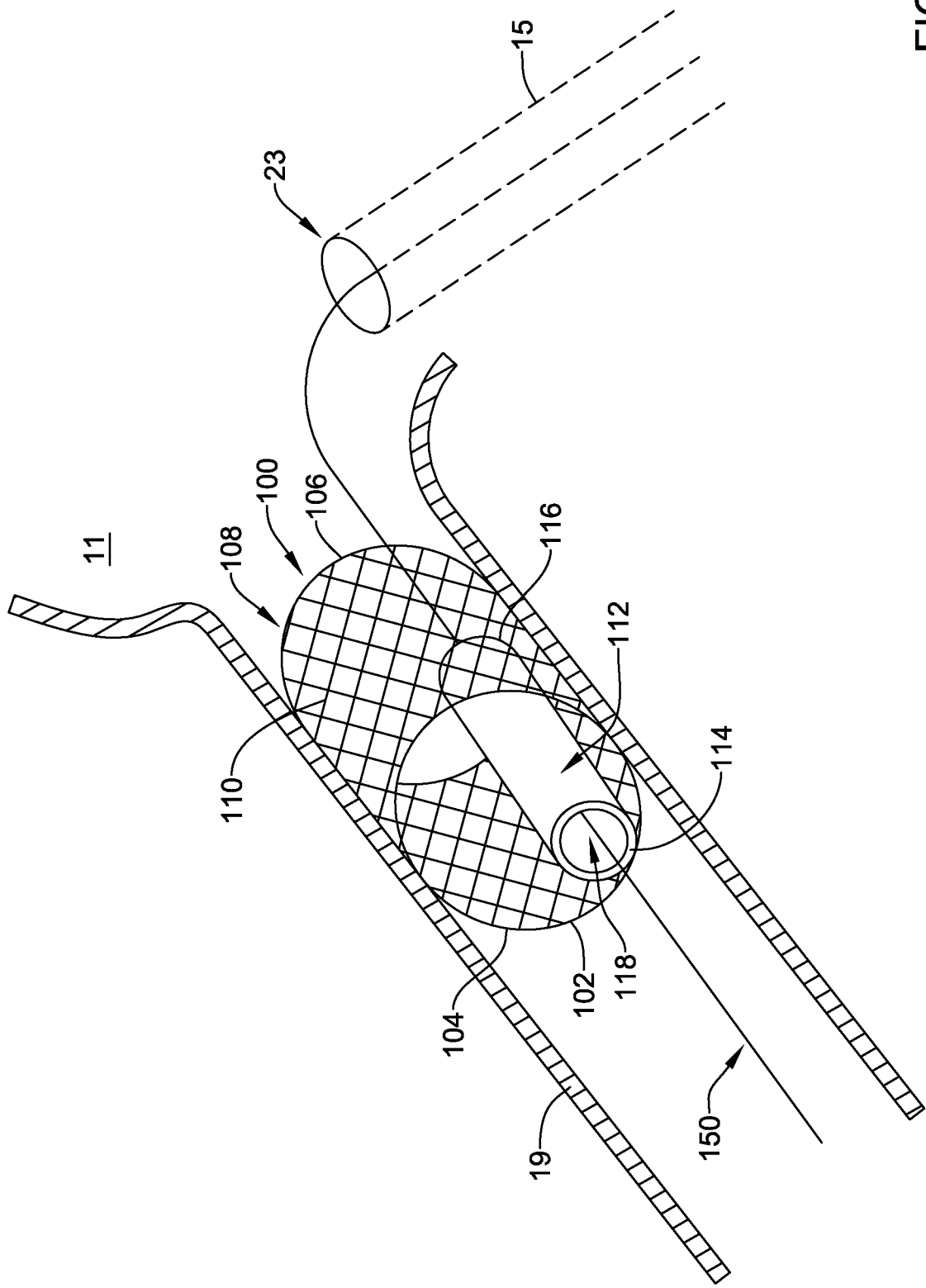
FIG. 5A is a schematic view of another illustrative expandable anchoring mechanism in an expanded configuration.

In some embodiments, it may desirable to deliver a fixation system separately from the leadless cardiac device. FIG. 5A illustrates a partial cross-sectional view of an illustrative fixation system or mechanism 100 disposed in the IVC 19. While the system 100 is illustrated in the IVC 19, it should be understood the system 100 may be deployed in the SVC 21 or other vasculature, as desired. In some instances, the expandable anchoring mechanism 100 may be formed from an elongated tubular member or body 102 having a stent-like structure. While the expandable anchoring mechanism 100 is described as generally tubular, it is contemplated that the expandable anchoring mechanism 100 may take any cross-sectional shape desired. The expandable anchoring mechanism 100 may have a first, or proximal end 104 and a second, or distal end 106. The expandable anchoring mechanism 100 may include a lumen 108 extending from a first opening adjacent the first end 104 to a second opening adjacent to the second end 106 to allow for the passage of blood, fluids, etc.

The expandable anchoring mechanism 100 may be expandable from a first radially collapsed configuration (not explicitly shown) to a second radially expanded configuration. In some cases, the expandable anchoring mechanism 100 may be deployed to a configuration between the collapsed configuration and a fully expanded configuration. The expandable anchoring mechanism 100 may be structured to apply a radially outward pressure to the vessel wall to maintain the mechanism 100 and, if so coupled, the leadless cardiac device in the vessel.

The proximal end 104 of the expandable anchoring mechanism 100 may include a plurality of loops configured to receive a retrieval tether or suture (not explicitly shown) interwoven therethrough, or otherwise passing through one or more of the loops. The retrieval suture may be used to collapse and retrieve the expandable anchoring mechanism 100, if so desired. For example, the retrieval suture may be pulled like a drawstring to radially collapse the proximal end 104 of the expandable anchoring mechanism 100 to facilitate removal of the expandable anchoring mechanism 100 from a body lumen.

The expandable anchoring mechanism 100 may have a woven structure, fabricated from a number of filaments or struts 110. In some embodiments, the expandable anchoring mechanism 100 may be knitted or braided with a single filament interwoven with itself and defining open cells. In other embodiments, the expandable anchoring mechanism 100 may be braided with several filaments interwoven together and define open cells. Some exemplary stents including braided filaments include the WallFlex®, WALL-STENT®, and Polyflex® stents, made and distributed by Boston Scientific, Corporation. In another embodiment, the expandable anchoring mechanism 100 may be knitted, such as the Ultraflex™ stents made by Boston Scientific, Corporation. In yet another embodiment, the expandable anchoring mechanism 100 may be of a knotted type, such the Precision Colonic™ stents made by Boston Scientific, Corporation. In still another embodiment, the expandable anchoring mechanism 100 may be a laser cut tubular member, such as the EPIC™ stents made by Boston Scientific, Corporation. A laser cut tubular member may have an open and/or closed cell geometry including one or more interconnected filaments or struts defining open cells therebetween. In some instances, an inner and/or outer surface of the expandable anchoring mechanism 100 may be entirely, substantially or partially, covered with a polymeric covering or coating. The covering or coating may extend across and/or occlude one or more, or a plurality of the cells defined by the struts or filaments 110. The covering or coating may help reduce tissue ingrowth. In some cases, the expandable anchoring mechanism 100 may be a self-expanding stent (SES), although this is not required.

Figure 5B:
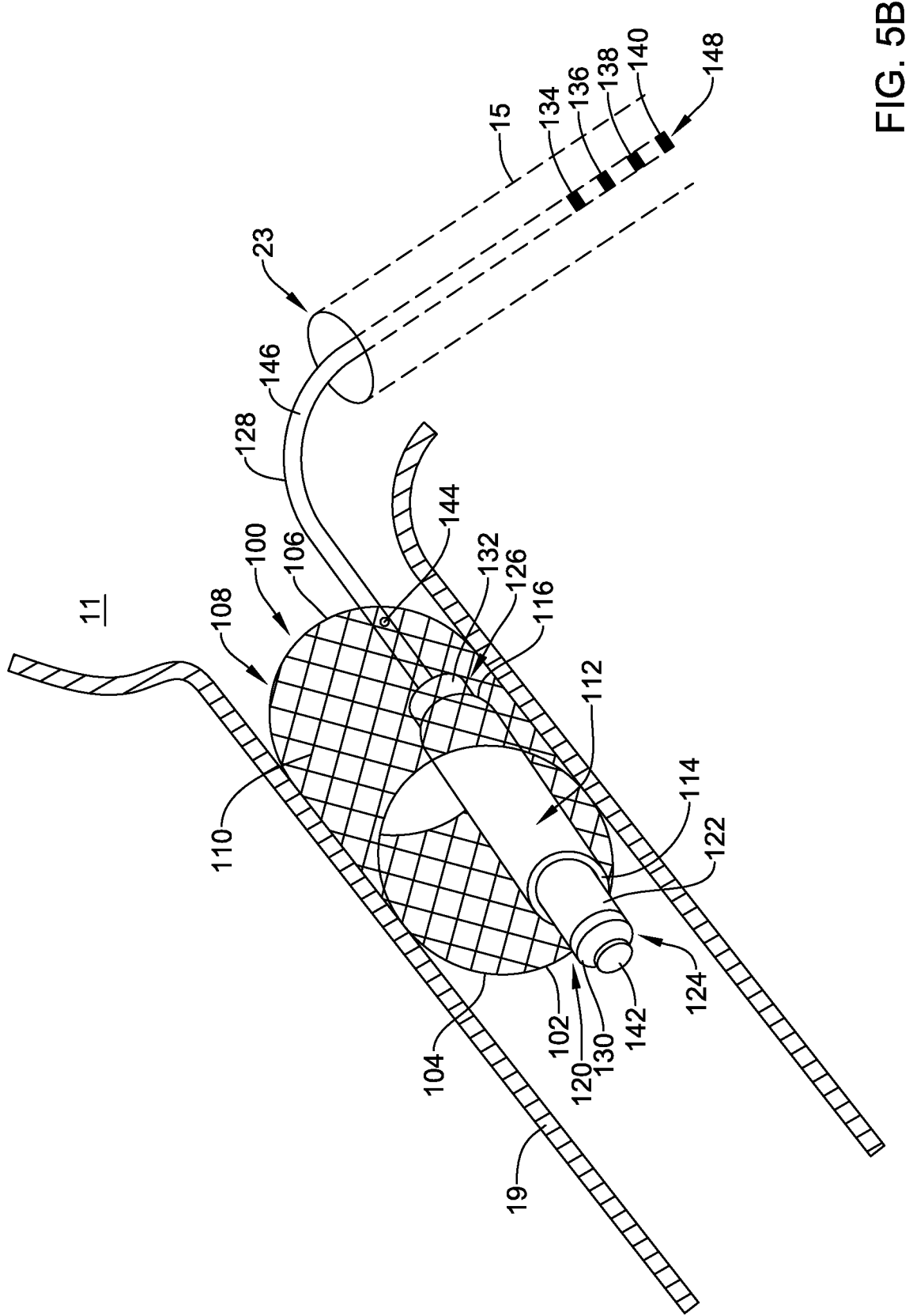
FIG. 5B is a schematic view of the expandable anchoring mechanism of FIG. 5A with an illustrative leadless pacing device.

The expandable anchor mechanism 100 may further include an elongated tubular member or dock 112 coupled to the body 102 within the lumen 108 thereof. The dock 112 may be coupled to the body 102 using any suitable method such as, but not limited to welding, brazing, soldering, adhesives, melt bonding, etc. While the dock 112 is described as generally tubular, it is contemplated that the dock 112 may take any cross-sectional shape desired. The dock 112 may have a first, or proximal end 114 and a second, or distal end 116. The dock 112 may include a lumen 118 extending from a first opening adjacent the first end 114 to a second opening adjacent to the second end 116 to receive a leadless pacing device 120, as shown in FIG. 5B. The lumen 118 may be further configured to receive a guidewire 150 to facilitate delivery of the expandable anchor mechanism 100 and/or leadless cardiac device 120, as will be described in more detail herein. For example, the guidewire 150 may be used to direct a distal extension 128 (see, for example, FIG. 5B) into the coronary sinus 15 through the coronary sinus ostium 16. In some cases, the dock 112 may be provided with a second smaller tubular member (e.g., a side car) defining a lumen and configured to receive the guidewire 150.

The dock 112 may be formed from a flexible and/or elastomeric material (for example, silicone) such that the leadless pacing device 120 may be inserted into the lumen 118 with an interference and/or friction fit. In other words, the diameter of the lumen 118 may be about the same size as, or slightly smaller than, an outer diameter of the leadless pacing device 120. Alternatively, or additionally, the dock 112 and/or leadless cardiac device 120 may include mechanical interfaces that releasably or fixedly couple the leadless cardiac device 120 to the dock 112. Further, while the dock 112 is illustrated as a substantially solid tubular member, it is contemplated that the dock 112 may have a stent-like structure similar to the body 102.

FIG. 5B illustrates a partial cross-sectional view of an illustrative fixation system 100 disposed in the IVC 19 with an illustrative leadless cardiac device 120 disposed within the lumen 118 of the dock 112. The leadless cardiac device 120 may be similar in form and function to the leadless pacing device 20 described above. The leadless pacing device 120 includes a housing 122 having a proximal end 124 and a distal end 126 and a distal extension 128 extending distally of the distal end 126 of the housing 122. In some embodiments, the leadless pacing device 120 may additionally include one or more electrodes. In one example, the housing 122 may support a first electrode 130 and a second electrode 132, while the distal extension 128 may support a distal electrode. In some cases, the distal electrode may include a plurality of electrodes (e.g., a first proximal ring electrode 134, a second proximal ring electrode 136, a third proximal ring electrode 138, a distal ring electrode 140, and/or one or more other electrodes). Although the electrodes described may be indicated as being ring electrodes, other electrode types may be utilized depending on the application.

In some instances, the housing 122 may include a proximal member 142 (e.g., a docking hub or other member) which extends generally from the proximal end of the housing 122. In the example shown in FIG. 5B, the proximal member 142 may extend from the proximal end 124 of the housing 122. During implantation, the proximal member 142 may be releasably coupled to a positioning device (not shown in FIG. 5B). When coupled, movement of the positioning device may translate to the housing 122, thereby allowing a user, such as a physician, to maneuver the housing 122 into a proper position within the heart 10, for example into or proximate the IVC 19. Alternatively, or additionally, the proximal member 142 may be configured to facilitate retrieval of the leadless pacing device 120, as desired.

The distal extension 128 is illustrated as entering the coronary sinus 15 via the ostium 16 such that the electrodes 134-140 are positioned within the coronary sinus 15. However, the distal extension 128 may be positioned within the right atrium 11, great cardiac vein 17, and/or distal branch veins, as desired. To facilitate placement of the distal extension 128, the distal extension 128 may include a side port 144 configured to allow a guidewire (such as guidewire 150) or a stylet to enter a lumen 146 of the distal extension 128. The lumen 146 may extend from the side port 144 to a distal opening 148 adjacent a distal end of the distal extension 128. In some cases, the lumen 146 may terminate at a location proximal to the distal end of the distal extension 128 such that a stop or wall may be provided in which a stylet may exert a pushing force.

It is contemplated that the leadless cardiac device 120 may be extracted or removed from the expandable anchor mechanism 100, if so desired. In some cases, the leadless cardiac device 120 and distal extension 128 may be removed by using a snare to grab or attach to the proximal member 142 and exerting a proximal pulling force. The proximal pulling force may retract the leadless cardiac device 120 from the dock 112 with manual traction. In some cases, the expandable anchor mechanism 100 may also be removed by collapsing the body 102 thereof and proximally retracting. However, in some cases, it may not be possible or desirable to remove expandable anchor mechanism 100. It is contemplated that the dock 112 and the leadless cardiac device 120 may be removed together. For example a cutting tool or laser may be use to uncouple the dock from the expandable anchor mechanism 100 and the leadless cardiac device 120 and dock 112 removed together. In such an instance, the leadless cardiac device 120 and the dock112 may be removed while the body 102 is left in the vessel.

Figure 6:
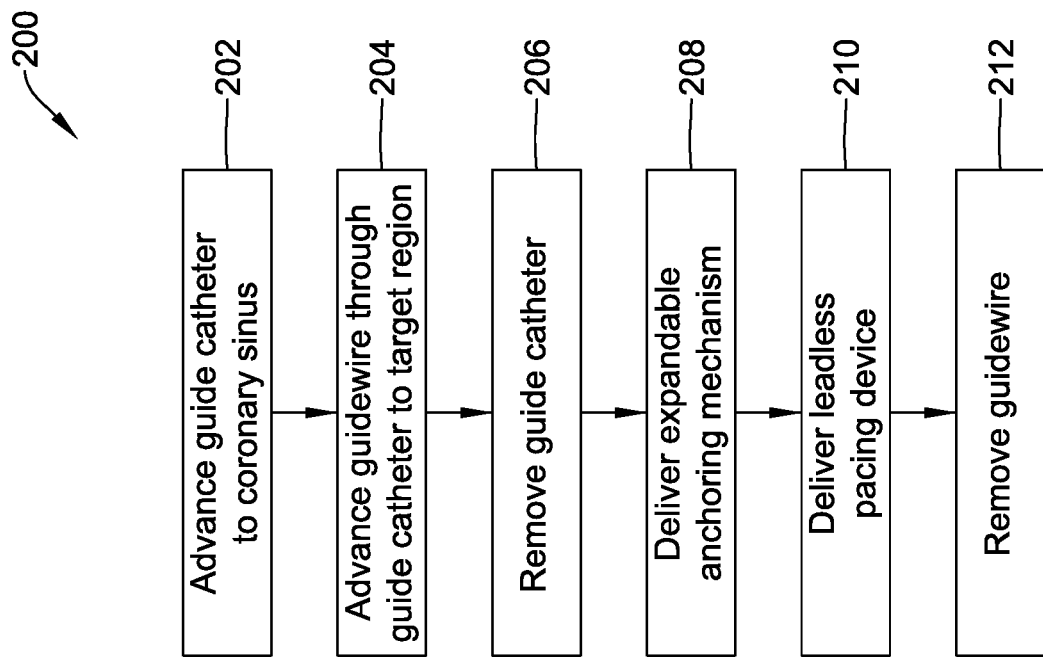
FIG. 6 is a flow chart of an illustrative method for deploying an illustrative leadless pacing device.

FIG. 6 is a flow chart of an illustrative method 200 for separately (e.g., in succession) an expandable anchor mechanism 100 and a leadless cardiac device 120. To begin, a guide catheter may be advanced through the vasculature and to the coronary sinus, as indicated at step 202. The guide catheter may be advanced through the SVC, into the right atrium, and into the coronary sinus ostium using a superior approach accessed through the internal jugular vein or the subclavian vein. Alternatively, the guide catheter may be advanced through the IVC, into the right atrium, and into the coronary sinus ostium using an inferior approach accessed through the femoral vein. It is contemplated that the approach selected (e.g., inferior or superior) will determine the implantation location of the leadless cardiac device 120. Once the guide catheter has cannulated the coronary sinus, a guidewire 150 may be advanced through the guide catheter, as shown at step 204. The guidewire 150 may be advanced distally beyond a distal end of the guide catheter to a target region. In some cases, the target region may be a desired location for a distal end of the distal extension 128 within the coronary sinus or a distal branch thereof. Once the guidewire 150 is positioned, the guide catheter may be removed, as shown at step 206. The expandable anchor mechanism 100 may then be advanced over the guidewire 150, as shown at step 208. For example, the dock 112 or side car, if so provided) may be slidably disposed over the guidewire 150. Delivery of the expandable anchor mechanism 100 may require a delivery catheter configured to maintain the body 102 in a collapsed configuration until the expandable anchor mechanism 100 is at the target location within the IVC or SVC. In some cases, the expandable anchor mechanism 100 may include radiopaque materials and/or markers configured to facilitate deployment and positioning thereof. Once the expandable anchor mechanism 100 has been delivered (and the delivery catheter removed, if used), the leadless cardiac device 120 may then be delivered over the guidewire 150, as shown at step 210. The distal extension 128 may be positioned over the guidewire 150 using the lumen 146 and side port 144 and advanced until the distal extension 128 is in the desired position. As the distal extension 128 is guided to its target location, the housing 122 of the leadless cardiac device 120 may be inserted into and anchored within the lumen 118 of the dock 112. Once the distal extension 128 and housing 122 are in position and coupled or fixated in place, the guidewire 150 (and any other delivery components) may be removed, as shown at step 212.

Figure 7:
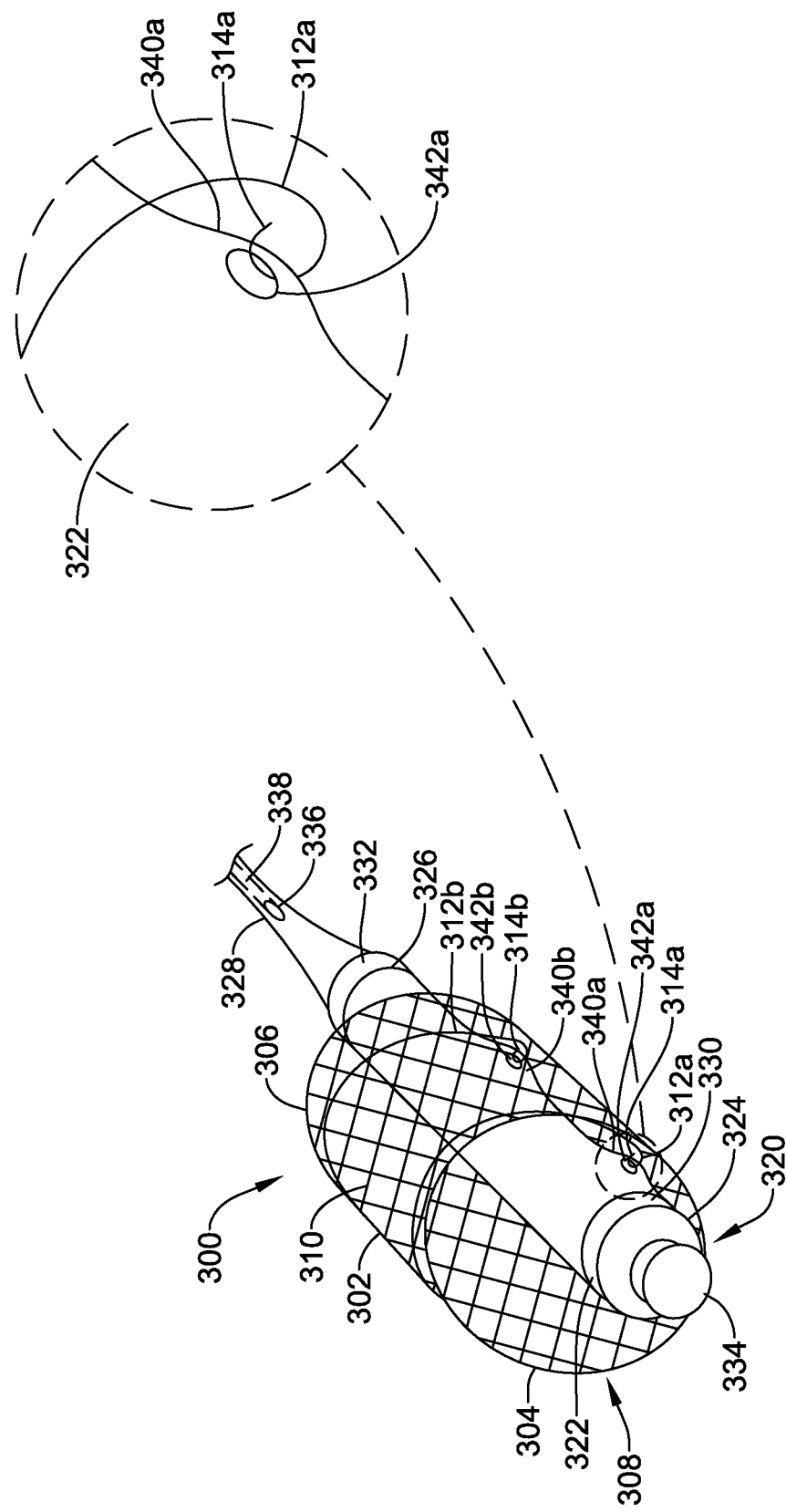
FIG. 7 is schematic view of another illustrative expandable anchoring mechanism with an illustrative leadless pacing device.

FIG. 7 illustrates a perspective view of another illustrative expandable anchoring system or mechanism 300 and leadless cardiac device 320 where the leadless cardiac device 320 is removable from the expandable anchor mechanism 300. The system 300 may be deployed in the IVC 19, SVC 21 or other vasculature, as desired. In some instances, the expandable anchoring mechanism 300 may be similar in form and function to the expandable anchoring mechanism 100 described above. The expandable anchor mechanism 300 may be formed from an elongated tubular member or body 302 having a stent-like structure. While the expandable anchoring mechanism 300 is described as generally tubular, it is contemplated that the expandable anchoring mechanism 300 may take any cross-sectional shape desired. The expandable anchoring mechanism 300 may have a first, or proximal end 304 and a second, or distal end 306. The expandable anchoring mechanism 300 may include a lumen 308 extending from a first opening adjacent the first end 304 to a second opening adjacent to the second end 306 to allow for the passage of blood, fluids, etc.

The expandable anchoring mechanism 300 may be expandable from a first radially collapsed configuration (not explicitly shown) to a second radially expanded configuration. In some cases, the expandable anchoring mechanism 300 may be deployed to a configuration between the collapsed configuration and a fully expanded configuration. The expandable anchoring mechanism 300 may be structured to apply a radially outward pressure to the vessel wall to maintain the mechanism 300 and, if so coupled, the leadless cardiac device in the vessel.

The expandable anchoring mechanism 300 may have a woven structure, fabricated from a number of filaments or struts 310. In some embodiments, the expandable anchoring mechanism 300 may be knitted or braided with a single filament interwoven with itself and defining open cells. In other embodiments, the expandable anchoring mechanism 300 may be braided with several filaments interwoven together and define open cells. In yet another embodiment, the expandable anchoring mechanism 300 may be of a knotted type. In still another embodiment, the expandable anchoring mechanism 300 may be a laser cut tubular member. In some instances, an inner and/or outer surface of the expandable anchoring mechanism 300 may be entirely, substantially or partially, covered with a polymeric covering or coating. The covering or coating may extend across and/or occlude one or more, or a plurality of the cells defined by the struts or filaments 310. The covering or coating may help reduce tissue ingrowth. In some cases, the expandable anchoring mechanism 300 may be a self-expanding stent (SES), although this is not required.

The expandable anchor mechanism 300 may further include one or more struts or wires 312a, 312b (collectively, 312) each configured to engage a mating feature on the leadless cardiac device 320 to releasbly couple the leadless cardiac device 320 to the expandable anchor mechanism 300. In some cases, the wires 312 may be one or more filaments from the body 302. In another example, the wires 312 may be a separately attached structure. The wires 312a, 312b may each having a free end 314a, 314b configured to engage the leadless cardiac device 320, as will be described in more detail below.

The leadless cardiac device 320 may be similar in form and function to the leadless pacing devices 20, 120 described above. The leadless pacing device 320 includes a housing 322 having a proximal end 324 and a distal end 326 and a distal extension 328 extending distally of the distal end 326 of the housing 322. In some embodiments, the leadless pacing device 320 may additionally include one or more electrodes. In one example, the housing 322 may support a first electrode 330 and a second electrode 332, while the distal extension 328 may support a distal electrode. In some cases, the distal electrode may include a plurality of electrodes (not explicitly shown). Although the electrodes described may be indicated as being ring electrodes, other electrode types may be utilized depending on the application.

In some instances, the housing 322 may include a proximal member 334 (e.g., a docking hub or other member) which extends generally from the proximal end of the housing 322. In the example shown in FIG. 7, the proximal member 334 may extend from the proximal end 324 of the housing 322. During implantation, the proximal member 334 may be releasably coupled to a positioning device (not shown in FIG. 7). When coupled, movement of the positioning device may translate to the housing 322, thereby allowing a user, such as a physician, to maneuver the housing 322 into a proper position within the heart 10, for example into or proximate the IVC 19. Alternatively, or additionally, the proximal member 334 may be configured to facilitate retrieval of the leadless pacing device 320, as desired.

The distal extension 328 may be positioned within the coronary sinus 15, right atrium 11, great cardiac vein 17, and/or distal branch veins, as desired. To facilitate placement of the distal extension 328, the distal extension 328 may include a side port 336 configured to allow a guidewire or a stylet to enter a lumen 338 of the distal extension 328. The lumen 338 may extend from the side port 336 to a distal opening adjacent a distal end (not explicitly shown) of the distal extension 328. In some cases, the lumen 338 may terminate at a location proximal to the distal end of the distal extension 328 such that a stop or wall may be provided in which a stylet may exert a pushing force.

The leadless cardiac device 320 may include one or more generally flat shelf-like portions 340a, 340b (collectively, 340) extending from the generally cylindrical housing 322. Each of the extensions 340a, 340b may include a hole or apertures 342a, 342b (collectively, 342) extending therethrough. The apertures 342 may be configured to receive the free end 314 of the wire 312. While the expandable anchor mechanism 300 is illustrated as including two wires 312 configured to engage two apertures 342 on the leadless cardiac device 320, it is contemplated that the expandable anchor mechanism 300 and/or leadless cardiac device 320 may each include any number of coupling features such as, but not limited to, one, two, three, four, or more. In some cases, a first set of coupling features 312a, 342a may be positioned near a proximal end 324 of the leadless cardiac device 320 and a second set of coupling features 312b, 342b may be positioned near a distal end 326 of the leadless cardiac device 320. This may help maintain the leadless cardiac device 320 in close alignment with the vessel wall, if so desired.

It is contemplated that the free end 314 of the wire 312 may be curved such that once engaged with the apertures 342, the leadless cardiac device 320 can be removed with an intentional applied force while preventing or minimizing unintentional uncoupling. For example, the leadless cardiac device 320 may be removed from the expandable anchor mechanism 300 by rotating the leadless cardiac device 320 in a counter-clockwise direction (e.g., in a direction opposite to the rotation of the free end 314). As the leadless cardiac device 320 is rotated, the apertures 342 slide along the wire 312 until it disengages from the wire 312. In some cases, the wire 312 may flex or uncoil as the leadless cardiac device 320 is rotated. It is contemplated that a snare or customized catheter may be use to grip the proximal member 334 and then used to rotate the leadless cardiac device 320. Once the leadless cardiac device 320 has been disengaged form the body 302, the leadless cardiac device 320 may be removed and the expandable anchor mechanism 300 may remain in the body.

It is contemplated that the expandable anchor mechanism 300 and the leadless cardiac device 320 may be delivered to the target location together or in succession, as desired. In a first example, the leadless cardiac device 320 may be loaded within the lumen 308 of the expandable anchor mechanism 300 prior to delivery within the body. The body 302 of the expandable anchor mechanism 300 may then be collapsed onto an outer surface of the housing 322 of the leadless cardiac device 320 for delivery. The expandable anchor mechanism 300 may be held in the collapsed using a delivery catheter, or other means for applying a biasing force on the expandable anchor mechanism 300. In another example, the expandable anchor mechanism 300 may be delivered and deployed within the body prior to coupling the leadless cardiac device 320 thereto. For example, the expandable anchor mechanism 300 and leadless cardiac device 320 may be delivered in succession. Once the expandable anchor mechanism 300 has been deployed, the leadless cardiac device 320 can be delivered and coupled to the expandable anchor mechanism 300. It is contemplated that the wires 312, free ends 314, and/or extensions of housing 340 may include radiopaque features configured to help a clinician align the apertures 342 with the free ends 314. The apertures 342 may be aligned with the free ends 314 and rotated in a same direction as the rotational direction of the wires 312 (e.g., clockwise in the illustrated embodiment) to couple the leadless cardiac device 320 with the expandable anchor mechanism 300.

Figure 8:
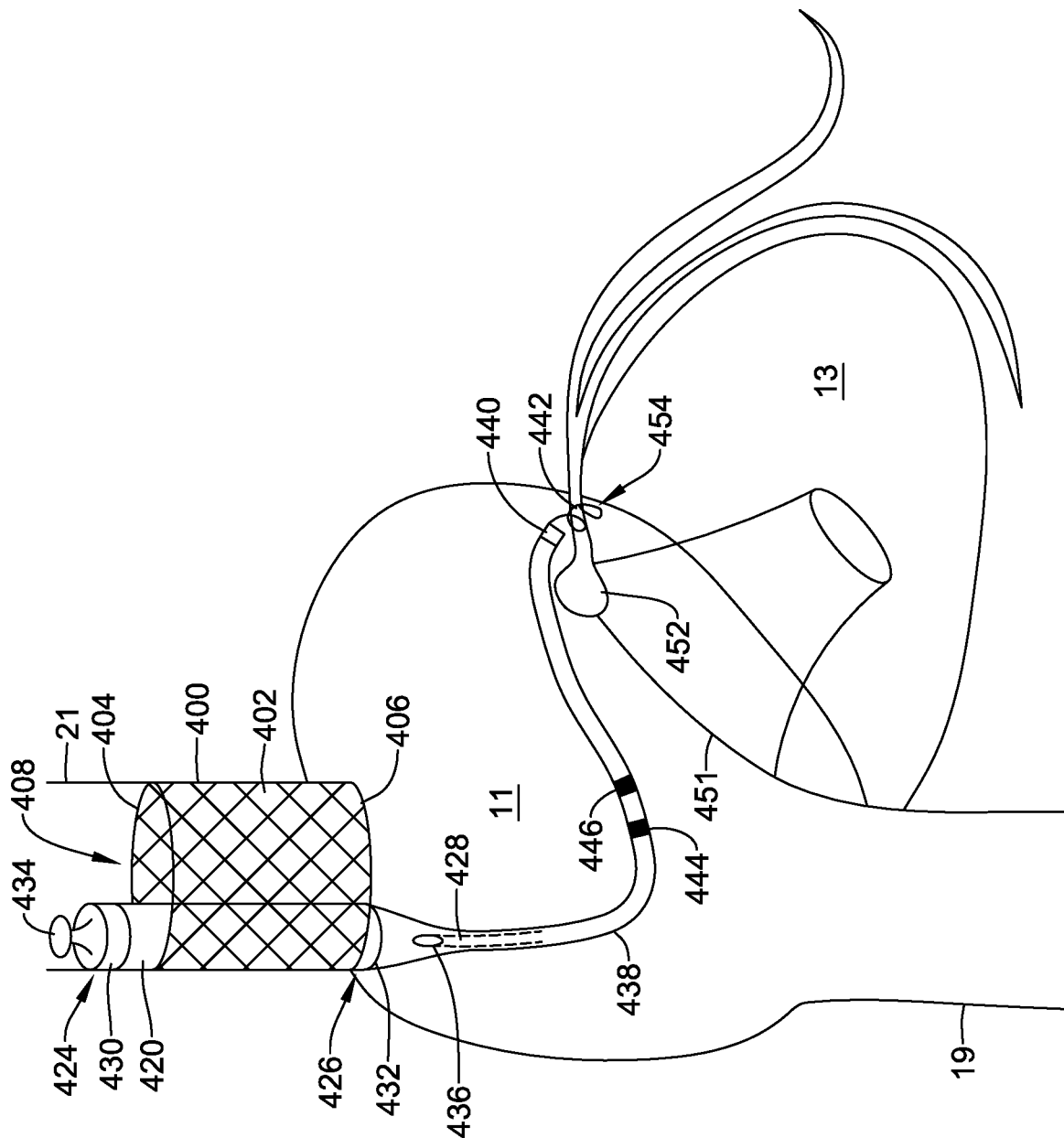
FIG. 8 is schematic view of another illustrative expandable anchoring mechanism with an illustrative leadless pacing device.

FIG. 8 illustrates a schematic view of another leadless cardiac device 420 having an expandable anchor mechanism 400 positioned within the SVC 21 with a distal extension 428 extending into the right atrium 11. While the expandable anchor mechanism 400 and leadless cardiac device 420 are illustrated in the SVC 21, it should be understood the expandable anchor mechanism 400 and leadless cardiac device 420 may be deployed in the IVC 19 or other vasculature, as desired. For example, the leadless cardiac device 420 may be positioned within the coronary sinus with the distal extension 428 extending into the right atrium 11. In some instances, the expandable anchoring mechanism 400 may be formed from an elongated tubular member or body 402 having a stent-like structure. However, the expandable anchor mechanism 400 may take any form desired. While the expandable anchoring mechanism 400 is described as generally tubular, it is contemplated that the expandable anchoring mechanism 400 may take any cross-sectional shape desired. The expandable anchoring mechanism 400 may have a first, or proximal end 404 and a second, or distal end 406. The expandable anchoring mechanism 400 may include a lumen 408 extending from a first opening adjacent the first end 404 to a second opening adjacent to the second end 406 to allow for the passage of blood, fluids, etc. The leadless cardiac device 420 may be fixedly or releasably coupled to the expandable anchor mechanism 400 using any of the structures and/or mechanisms described herein.

The expandable anchoring mechanism 400 may be expandable from a first radially collapsed configuration (not explicitly shown) to a second radially expanded configuration. In some cases, the expandable anchoring mechanism 400 may be deployed to a configuration between the collapsed configuration and a fully expanded configuration. The expandable anchoring mechanism 400 may be structured to apply a radially outward pressure to the vessel wall to maintain the mechanism 400 and, if so coupled, the leadless cardiac device in the vessel.

The proximal end 404 of the expandable anchoring mechanism 400 may include a plurality of loops configured to receive a retrieval tether or suture (not explicitly shown) interwoven therethrough, or otherwise passing through one or more of the loops. The retrieval suture may be used to collapse and retrieve the expandable anchoring mechanism 400, if so desired. For example, the retrieval suture may be pulled like a drawstring to radially collapse the proximal end 404 of the expandable anchoring mechanism 400 to facilitate removal of the expandable anchoring mechanism 400 from a body lumen.

The expandable anchoring mechanism 400 may have a woven structure, fabricated from a number of filaments or struts 410. In some embodiments, the expandable anchoring mechanism 400 may be knitted or braided with a single filament interwoven with itself and defining open cells. In other embodiments, the expandable anchoring mechanism 400 may be braided with several filaments interwoven together and define open cells. Some exemplary stents including braided filaments include the WallFlex®, WALL-STENT®, and Polyflex® stents, made and distributed by Boston Scientific, Corporation. In another embodiment, the expandable anchoring mechanism 400 may be knitted, such as the Ultraflex™ stents made by Boston Scientific, Corporation. In yet another embodiment, the expandable anchoring mechanism 400 may be of a knotted type, such the Precision Colonic™ stents made by Boston Scientific, Corporation. In still another embodiment, the expandable anchoring mechanism 400 may be a laser cut tubular member, such as the EPIC™ stents made by Boston Scientific, Corporation. A laser cut tubular member may have an open and/or closed cell geometry including one or more interconnected filaments or struts defining open cells therebetween. In some instances, an inner and/or outer surface of the expandable anchoring mechanism 400 may be entirely, substantially or partially, covered with a polymeric covering or coating. The covering or coating may extend across and/or occlude one or more, or a plurality of the cells defined by the struts or filaments 410. The covering or coating may help reduce tissue ingrowth. In some cases, the expandable anchoring mechanism 400 may be a self-expanding stent (SES), although this is not required.

The leadless cardiac device 420 may be similar in form and function to the leadless pacing devices 20, 120, 320 described above. The leadless pacing device 420 includes a housing 422 having a proximal end 424 and a distal end 426 and a distal extension 428 extending distally of the distal end 426 of the housing 422. In some embodiments, the leadless pacing device 420 may additionally include one or more electrodes. In one example, the housing 422 may support a first electrode 430 and a second electrode 432, while the distal extension 428 may support one or more distal electrodes 440, 442 and one or more intermediate electrodes 444, 446. Although the electrodes described may be indicated as being ring electrodes, other electrode types may be utilized depending on the application. It is contemplated that the distal electrodes 440, 442 may be configured to deliver pacing pulses to the Bundle of His 454 while the intermediate electrodes 444, 446 may be bipolar electrodes configured to sense activity in the right atrium. This may allow for VDD pacing in combination with His Bundle pacing. For example, one or both of the distal electrodes 440, 442 may be attached, fixated, secured, in contact with or otherwise coupled to the Bundle of His. In one example, at least one of the distal electrodes 442 may be configured to be fixated within and/or through a septal wall 18 (see, for example, FIG. 1) of the right atrium 11. In some cases, the distal electrode 442 may be fixated at a location above or near the tricuspid valve annulus 451, although other locations can be used.

In some instances, the housing 422 may include a proximal member 434 (e.g., a docking hub or other member) which extends generally from the proximal end of the housing 422. In the example shown in FIG. 8, the proximal member 434 may extend from the proximal end 424 of the housing 422. During implantation, the proximal member 434 may be releasably coupled to a positioning device (not shown in FIG. 8). When coupled, movement of the positioning device may translate to the housing 422, thereby allowing a user, such as a physician, to maneuver the housing 422 into a proper position within the heart 10, for example into or proximate the SVC 21. Alternatively, or additionally, the proximal member 434 may be configured to facilitate retrieval of the leadless pacing device 420, as desired.

The distal extension 428 may be positioned within the right atrium 11, coronary sinus 15, great cardiac vein 17, and/or distal branch veins, as desired. To facilitate placement of the distal extension 428, the distal extension 428 may include a side port 436 configured to allow a guidewire or a stylet to enter a lumen 438 of the distal extension 428. The lumen 438 may extend from the side port 436 to a distal opening adjacent a distal end of the distal extension 428. In some cases, the lumen 438 may terminate at a location proximal to the distal end of the distal extension 428 such that a stop or wall may be provided on which a stylet may exert a pushing force.

In the illustrated embodiment, the expandable anchoring mechanism 400 is illustrated in the expanded configuration with the housing 422 of the leadless cardiac device 420 engaging the vessel wall. However, it is contemplated that the expandable anchoring mechanism 400 may be configured to space the housing 422 of the leadless cardiac device 420 from the vessel wall. It is contemplated that the expandable anchor mechanism 300 and the leadless cardiac device 420 may be delivered to the target location together or in succession, as desired, using any of the methods described herein.

Figure 9:
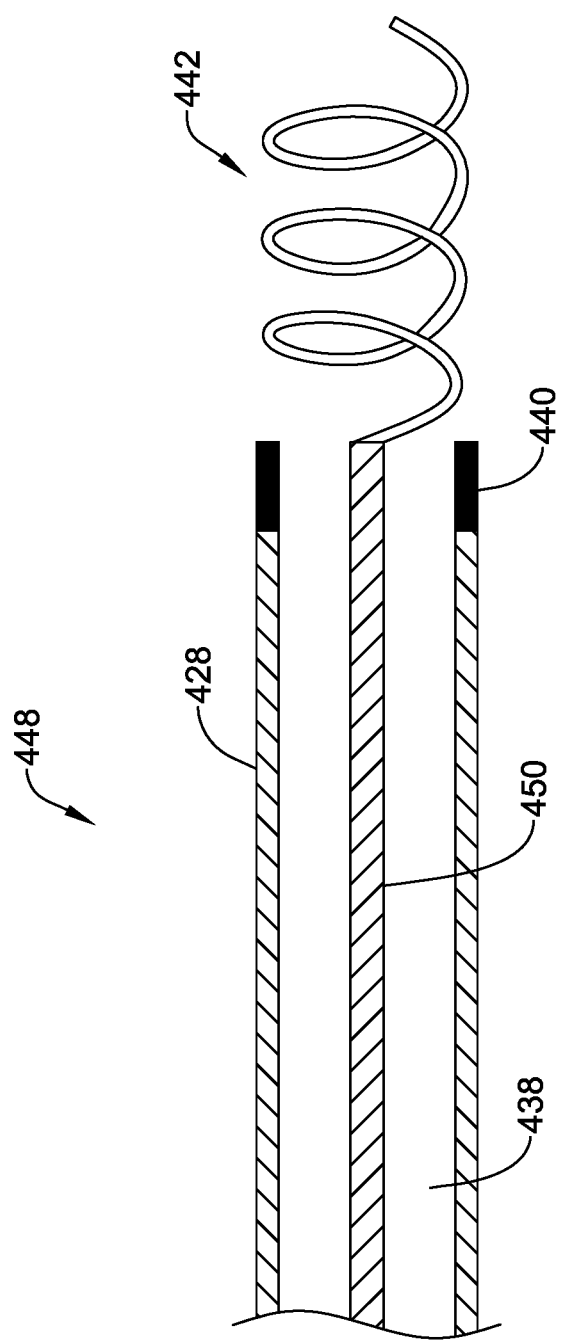
FIG. 9 is a schematic view of a distal electrode of FIG. 8.
Figure 10:
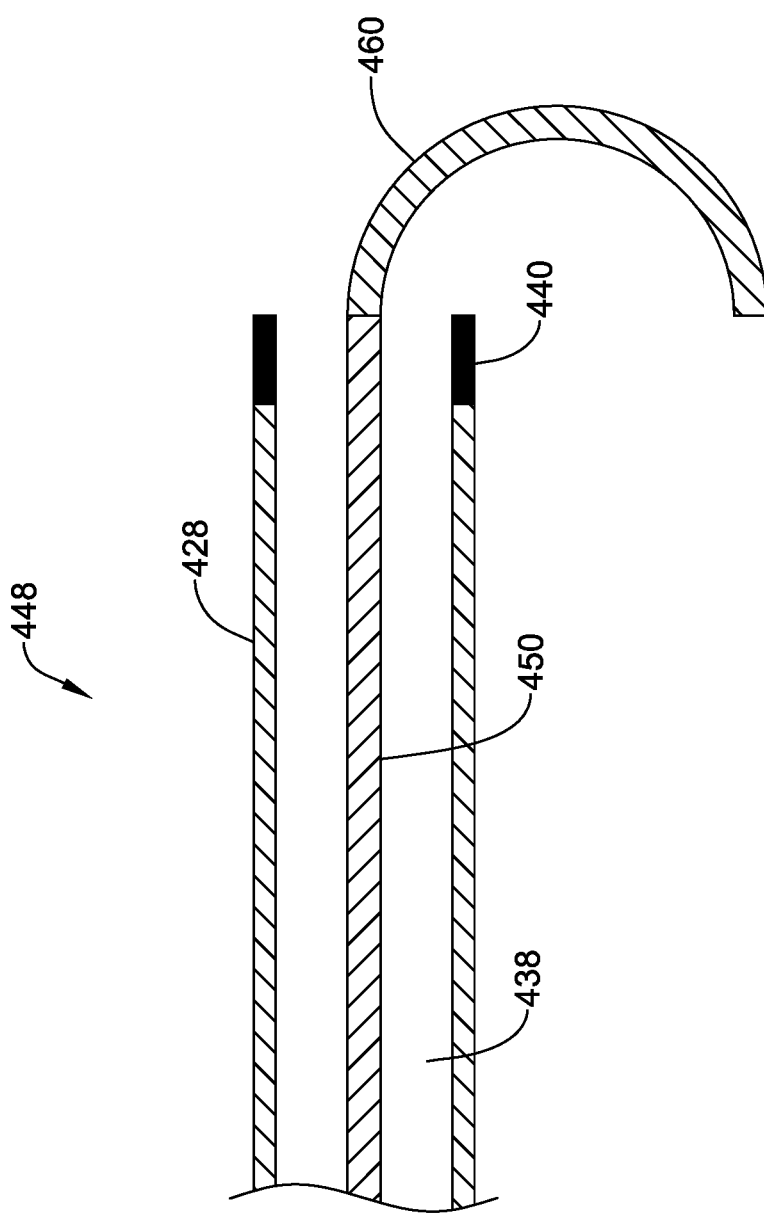
FIG. 10 is a schematic view of an alternative distal electrode of FIG. 8.

Referring additionally to FIG. 9, which illustrates a close up cross-sectional view of a distal end region 448 of the distal extension 428, in some cases, the distal electrode 442 may be an extendable and/or retractable helical cathode and configured to extend distally from the distal end of the distal extension 428. The electrode 442 may be controlled by a pre-loaded stylet 450 or actuation mechanism. The stylet 450 may be mechanically coupled to the distal electrode 442 such that it can effect longitudinal and rotation movement on the distal electrode 442. It is contemplated that the distal extension 428 may be advanced through the vasculature with the distal electrode 442 retracted within the lumen 438. In some cases, when retracted within the lumen 438, the electrode 442 may be biased into a straight or elongated configuration. In other cases, the distal electrode 442 may maintain its deployed shape when inside the lumen 438. The distal extension 428 may be advanced into the right atrium 11 until the distal end region 448 is positioned adjacent to the Bundle of His 454 which may be proximate the A-V node 452. The stylet 450 may be actuated to deploy the distal helical cathode 442 into the Bundle of His 454 (e.g., through or into a wall of the right atrium 11). In some cases, the stylet 450 may be rotated to drive the distal electrode 442 into the Bundle of His 454 in a manner similar to a screw. It is further contemplated that the stylet 450 may be curved, or otherwise shaped, such that as the distal electrode 442 is deployed it is simultaneously steered toward the desired deployment location (for example, away from the longitudinal axis of the distal extension 428. While the distal electrode is described as having a helical shape, it is contemplated that other shapes may also be used including, but limited to one or more curved hooks or one or more talons 460, as shown in FIG. 10 which illustrates a close up cross-sectional view of a distal end region 448 of the distal extension 428 having an alternative distal electrode 460. In some embodiments, a snare or lasso type device may be used to steer the distal end region 448 of the lead extension into place and release the distal electrode 460. It is contemplated that the distal electrode 460 may be formed from a shape memory material such that as it is deployed it assumes a curved configuration.

Figure 11:
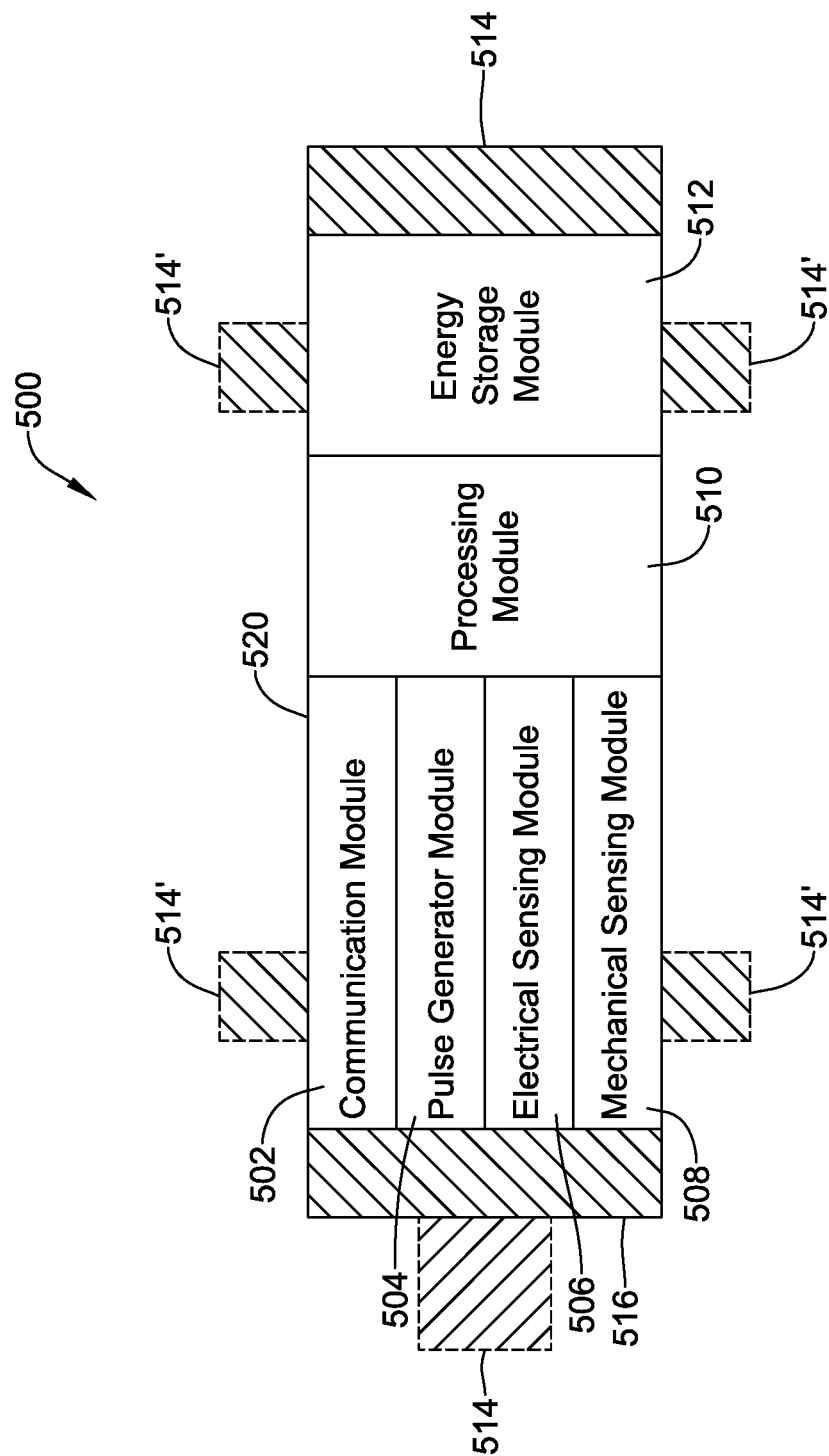
FIG. 11 is a schematic block diagram of an illustrative leadless cardiac device, which may be considered as being an example housing in one of the leadless cardiac devices described herein.

FIG. 11 is a conceptual schematic block diagram of an illustrative leadless cardiac device or leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 11, the LCP 500 may be a compact device with all components housed within the LCP 500 or directly on a housing 520. In some instances, the LCP 500 may include one or more of a communication module 502, a pulse generator module 504, an electrical sensing module 506, a mechanical sensing module 508, a processing module 510, an energy storage module 512, and electrodes 514.

The LCP 500 may be considered as an example of the housing that forms part of the leadless cardiac device 20 (FIGS. 1-4), leadless cardiac device 120 (FIGS. 5A-5B), leadless cardiac device 320 (FIG. 7), and/or leadless cardiac device 420 (FIG. 8). It will be appreciated that particular features or elements described with respect to one of the leadless cardiac device 20, the leadless cardiac device 120 leadless cardiac device 320, and/or leadless cardiac device 420 may be incorporated into any other of the leadless cardiac device 20, the leadless cardiac device 120 leadless cardiac device 320, and/or leadless cardiac device 420. Similarly, the particular features or elements described with respect to expandable anchoring mechanism 44, expandable anchor mechanism 100, expandable anchor mechanism 300, and/or expandable anchor mechanism 400 may be incorporated into any other of the expandable anchoring mechanism 44, expandable anchor mechanism 100, expandable anchor mechanism 300, and/or expandable anchor mechanism 400 or into any of the leadless cardiac device 20, the leadless cardiac device 120 leadless cardiac device 320, and/or leadless cardiac device 420.

As depicted in FIG. 11, the LCP 500 may include electrodes 514, which can be secured relative to the housing 520 and electrically exposed to tissue and/or blood surrounding the LCP 500. The electrodes 514 may generally conduct electrical signals to and from the LCP 500 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG). The electrodes 514 may include one or more biocompatible conductive materials such as various metals or alloys that are known to be safe for implantation within a human body. In some instances, the electrodes 514 may be generally disposed on either end of the LCP 500 and may be in electrical communication with one or more of modules the 502, 504, 506, 508, and 510. In embodiments where the electrodes 514 are secured directly to the housing 520, an insulative material may electrically isolate the electrodes 514 from adjacent electrodes, the housing 520, and/or other parts of the LCP 500. In some instances, some or all of the electrodes 514 may be spaced from the housing 520 and may be connected to the housing 520 and/or other components of the LCP 500 through connecting wires. In such instances, the electrodes 514 may be placed on a tail (not shown) that extends out away from the housing 520.

As shown in FIG. 11, in some embodiments, the LCP 500 may include electrodes 514'. The electrodes 514' may be in addition to the electrodes 514, or may replace one or more of the electrodes 514. The electrodes 514' may be similar to the electrodes 514 except that the electrodes 514' are disposed on the sides of the LCP 500. In some cases, the electrodes 514' may increase the number of electrodes by which the LCP 500 may deliver communication signals and/or electrical stimulation pulses, and/or may sense intrinsic cardiac electrical signals, communication signals, and/or electrical stimulation pulses. While generically shown as being the same size, it will be appreciated that one of the electrodes 514' may, for example, be relatively larger in surface area to be used as a pacing anode electrode while another of the electrodes 514' may be relatively smaller in surface area to be used as a pacing cathode electrode.

The electrodes 514 and/or 514' may assume any of a variety of sizes and/or shapes, and may be spaced at any of a variety of spacings. For example, the electrodes 514 may have an outer diameter of two to twenty millimeters (mm). In other embodiments, the electrodes 514 and/or 514' may have a diameter of two, three, five, seven millimeters (mm), or any other suitable diameter, dimension and/or shape. Example lengths for the electrodes 514 and/or 514' may include, for example, one, three, five, ten millimeters (mm), or any other suitable length. As used herein, the length is a dimension of the electrodes 514 and/or 514' that extends away from the outer surface of the housing 520. In some cases, the housing includes a protrusion (not shown) that extends away from the side of the housing, where the protrusion carries an anode electrode (e.g. electrode 514 or 514'). The protrusion may help space the anode electrode away from the side of the housing and into engagement with the patient's vasculature. In some instances, at least some of the electrodes 514 and/or 514' may be spaced from one another by a distance of twenty, thirty, forty, fifty millimeters (mm), or any other suitable spacing. The electrodes 514 and/or 514' of a single device may have different sizes with respect to each other, and the spacing and/or lengths of the electrodes on the device may or may not be uniform.

In the illustrative embodiment shown, the communication module 502 may be electrically coupled to the electrodes 514 and/or 514' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. The communication module 502 may additionally be configured to sense for communication signals delivered by other devices, which may be located external or internal to the patient's body.

The communication module 502 may communicate to help accomplish one or more desired functions. Some example functions include delivering sensed data, using communicated data for determining occurrences of events such as arrhythmias, coordinating delivery of electrical stimulation therapy, and/or other functions. In some cases, the LCP 500 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 500 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. In some cases, processed information may, for example, be provided by a chemical sensor or an optically interfaced sensor. Messages and/or commands may include instructions or the like directing another device to take action, notifications of imminent actions of the sending device, requests for reading from the receiving device, requests for writing data to the receiving device, information messages, and/or other messages commands.

In at least some embodiments, the communication module 502 (or the LCP 500) may further include switching circuitry to selectively connect one or more of the electrodes 514 and/or 514' to the communication module 502 in order to select which of the electrodes 514 and/or 514' that the communication module 502 delivers communication pulses with. It is contemplated that the communication module 502 may be communicating with other devices via conducted signals, radio frequency (RF) signals, optical signals, acoustic signals, inductive coupling, and/or any other suitable communication methodology. Where the communication module 502 generates electrical communication signals, the communication module 502 may include one or more capacitor elements and/or other charge storage devices to aid in generating and delivering communication signals. In the embodiment shown, the communication module 502 may use energy stored in the energy storage module 512 to generate the communication signals. In at least some examples, the communication module 502 may include a switching circuit that is connected to the energy storage module 512 and, with the switching circuitry, may connect the energy storage module 512 to one or more of the electrodes 514/514' to generate the communication signals.

As shown in FIG. 11, a pulse generator module 504 may be electrically connected to one or more of the electrodes 514 and/or 514'. The pulse generator module 504 may be configured to generate electrical stimulation pulses and deliver the electrical stimulation pulses to tissues of a patient via one or more of the electrodes 514 and/or 514' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 504 may generate electrical stimulation pacing pulses for capturing the heart of the patient, i.e. causing the heart to contract in response to the delivered electrical stimulation pulse. In some of these cases, the LCP 500 may vary the rate at which the pulse generator module 504 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. When used to treat other ailments, the pulse generator module 504 may generate electrical stimulation pulses suitable for neurostimulation therapy or the like. The pulse generator module 504 may include one or more capacitor elements and/or other charge storage devices to aid in generating and delivering appropriate electrical stimulation pulses. In at least some embodiments, the pulse generator module 504 may use energy stored in the energy storage module 512 to generate the electrical stimulation pulses. In some particular embodiments, the pulse generator module 504 may include a switching circuit that is connected to the energy storage module 512 and may connect the energy storage module 512 to one or more of the electrodes 514/514' to generate electrical stimulation pulses.

The LCP 500 may further include an electrical sensing module 506 and a mechanical sensing module 508. The electrical sensing module 506 may be configured to sense intrinsic cardiac electrical signals conducted from the electrodes 514 and/or 514' to the electrical sensing module 506. For example, the electrical sensing module 506 may be electrically connected to one or more of the electrodes 514 and/or 514' and the electrical sensing module 506 may be configured to receive cardiac electrical signals conducted through the electrodes 514 and/or 514' via a sensor amplifier or the like. In some embodiments, the cardiac electrical signals may represent local information from the chamber in which the LCP 500 is implanted. For instance, if the LCP 500 is implanted within a ventricle of the heart, cardiac electrical signals sensed by the LCP 500 through the electrodes 514 and/or 514' may represent ventricular cardiac electrical signals. The mechanical sensing module 508 may include, or be electrically connected to, various sensors, such as accelerometers, including multi-axis accelerometers such as two- or three-axis accelerometers, gyroscopes, including multi-axis gyroscopes such as two- or three-axis gyroscopes, blood pressure sensors, heart sound sensors, piezoelectric sensors, blood-oxygen sensors, and/or other sensors which measure one or more physiological parameters of the heart and/or patient. Mechanical sensing module 508, when present, may gather signals from the sensors indicative of the various physiological parameters. The electrical sensing module 506 and the mechanical sensing module 508 may both be connected to the processing module 510 and may provide signals representative of the sensed cardiac electrical signals and/or physiological signals to the processing module 510. Although described with respect to FIG. 11 as separate sensing modules, in some embodiments, the electrical sensing module 506 and the mechanical sensing module 508 may be combined into a single module. In at least some examples, the LCP 500 may only include one of the electrical sensing module 506 and the mechanical sensing module 508. In some cases, any combination of the processing module 510, the electrical sensing module 506, the mechanical sensing module 508, the communication module 502, the pulse generator module 504 and/or the energy storage module may be considered a controller of the LCP 500.

The processing module 510 may be configured to direct the operation of the LCP 500 and may, in some embodiments, be termed a controller. For example, the processing module 510 may be configured to receive cardiac electrical signals from the electrical sensing module 506 and/or physiological signals from the mechanical sensing module 508. Based on the received signals, the processing module 510 may determine, for example, occurrences and types of arrhythmias and other determinations such as whether the LCP 500 has become dislodged. The processing module 510 may further receive information from the communication module 502. In some embodiments, the processing module 510 may additionally use such received information to determine occurrences and types of arrhythmias and/or and other determinations such as whether the LCP 500 has become dislodged. In still some additional embodiments, the LCP 500 may use the received information instead of the signals received from the electrical sensing module 506 and/or the mechanical sensing module 508—for instance if the received information is deemed to be more accurate than the signals received from the electrical sensing module 506 and/or the mechanical sensing module 508 or if the electrical sensing module 506 and/or the mechanical sensing module 508 have been disabled or omitted from the LCP 500.

After determining an occurrence of an arrhythmia, the processing module 510 may control the pulse generator module 504 to generate electrical stimulation pulses in accordance with one or more electrical stimulation therapies to treat the determined arrhythmia. For example, the processing module 510 may control the pulse generator module 504 to generate pacing pulses with varying parameters and in different sequences to effectuate one or more electrical stimulation therapies. As one example, in controlling the pulse generator module 504 to deliver bradycardia pacing therapy, the processing module 510 may control the pulse generator module 504 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, the processing module 510 may monitor one or more physiological parameters of the patient which may indicate a need for an increased heart rate (e.g. due to increased metabolic demand). The processing module 510 may then increase the rate at which the pulse generator module 504 generates electrical stimulation pulses. Adjusting the rate of delivery of the electrical stimulation pulses based on the one or more physiological parameters may extend the battery life of the LCP 500 by only requiring higher rates of delivery of electrical stimulation pulses when the physiological parameters indicate there is a need for increased cardiac output. Additionally, adjusting the rate of delivery of the electrical stimulation pulses may increase a comfort level of the patient by more closely matching the rate of delivery of electrical stimulation pulses with the cardiac output need of the patient.

For ATP therapy, the processing module 510 may control the pulse generator module 504 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, the processing module 510 may control the pulse generator module 504 to reduce the rate of delivered pacing pulses down to a safer level. In CRT, the processing module 510 may control the pulse generator module 504 to deliver pacing pulses in coordination with another device to cause the heart to contract more efficiently. In cases where the pulse generator module 504 is capable of generating defibrillation and/or cardioversion pulses for defibrillation/cardioversion therapy, the processing module 510 may control the pulse generator module 504 to generate such defibrillation and/or cardioversion pulses. In some cases, the processing module 510 may control the pulse generator module 504 to generate electrical stimulation pulses to provide electrical stimulation therapies different than those examples described above.

Aside from controlling the pulse generator module 504 to generate different types of electrical stimulation pulses and in different sequences, in some embodiments, the processing module 510 may also control the pulse generator module 504 to generate the various electrical stimulation pulses with varying pulse parameters. For example, each electrical stimulation pulse may have a pulse width and a pulse amplitude. The processing module 510 may control the pulse generator module 504 to generate the various electrical stimulation pulses with specific pulse widths and pulse amplitudes. For example, the processing module 510 may cause the pulse generator module 504 to adjust the pulse width and/or the pulse amplitude of electrical stimulation pulses if the electrical stimulation pulses are not effectively capturing the heart. Such control of the specific parameters of the various electrical stimulation pulses may help the LCP 500 provide more effective delivery of electrical stimulation therapy.

In some embodiments, the processing module 510 may further control the communication module 502 to send information to other devices. For example, the processing module 510 may control the communication module 502 to generate one or more communication signals for communicating with other devices of a system of devices. For instance, the processing module 510 may control the communication module 502 to generate communication signals in particular pulse sequences, where the specific sequences convey different information. The communication module 502 may also receive communication signals for potential action by the processing module 510.

In further embodiments, the processing module 510 may control switching circuitry by which the communication module 502 and the pulse generator module 504 deliver communication signals and/or electrical stimulation pulses to tissue of the patient. As described above, both the communication module 502 and the pulse generator module 504 may include circuitry for connecting one or more of the electrodes 514 and/or 514' to the communication module 502 and/or the pulse generator module 504 so those modules may deliver the communication signals and electrical stimulation pulses to tissue of the patient. The specific combination of one or more electrodes by which the communication module 502 and/or the pulse generator module 504 deliver communication signals and electrical stimulation pulses may influence the reception of communication signals and/or the effectiveness of electrical stimulation pulses. Although it was described that each of the communication module 502 and the pulse generator module 504 may include switching circuitry, in some embodiments, the LCP 500 may have a single switching module connected to the communication module 502, the pulse generator module 504, and the electrodes 514 and/or 514'. In such embodiments, processing module 510 may control the switching module to connect the modules 502/504 and the electrodes 514/514' as appropriate.

In some embodiments, the processing module 510 may include a pre-programmed chip, such as a very-large-scale integration (VLSI) chip or an application specific integrated circuit (ASIC). In such embodiments, the chip may be pre-programmed with control logic in order to control the operation of the LCP 500. By using a pre-programmed chip, the processing module 510 may use less power than other programmable circuits while able to maintain basic functionality, thereby potentially increasing the battery life of the LCP 500. In other instances, the processing module 510 may include a programmable microprocessor or the like. Such a programmable microprocessor may allow a user to adjust the control logic of the LCP 500 after manufacture, thereby allowing for greater flexibility of the LCP 500 than when using a pre-programmed chip. In still other embodiments, the processing module 510 may not be a single component. For example, the processing module 510 may include multiple components positioned at disparate locations within the LCP 500 in order to perform the various described functions. For example, certain functions may be performed in one component of the processing module 510, while other functions are performed in a separate component of the processing module 510.

The processing module 510, in additional embodiments, may include a memory circuit and the processing module 510 may store information on and read information from the memory circuit. In other embodiments, the LCP 500 may include a separate memory circuit (not shown) that is in communication with the processing module 510, such that the processing module 510 may read and write information to and from the separate memory circuit. The memory circuit, whether part of the processing module 510 or separate from the processing module 510, may be volatile memory, non-volatile memory, or a combination of volatile memory and non-volatile memory.

The energy storage module 512 may provide a power source to the LCP 500 for its operations. In some embodiments, the energy storage module 512 may be a non-rechargeable lithium-based battery. In other embodiments, the non-rechargeable battery may be made from other suitable materials. In some embodiments, the energy storage module 512 may be considered to be a rechargeable power supply, such as but not limited to, a rechargeable battery. In still other embodiments, the energy storage module 512 may include other types of energy storage devices such as capacitors or super capacitors. In some cases, as will be discussed, the energy storage module 512 may include a rechargeable primary battery and a non-rechargeable secondary battery. In some cases, the primary battery and the second battery, if present, may both be rechargeable.

The expandable anchoring mechanisms described herein, such as the expandable anchoring mechanisms 44, 100, 300, 400, or other components disclosed herein, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In some cases, an expandable anchoring mechanism such as the expandable anchoring mechanism 44, 100, 300, 400, or other components disclosed herein, may be formed of, coated with or otherwise include one or more polymeric materials. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. A cardiac device configured for deployment within a patient's vasculature at a location near the patient's heart, the cardiac device comprising:
    an elongated housing configured to be positioned within the patient's vasculature proximate the patient's heart, the elongated housing having a proximal end and a distal end;
    a power source disposed within the elongated housing;
    circuitry disposed within the elongated housing and operatively coupled to the power source, the circuitry configured to pace the patient's heart and/or sense electrical activity of the patient's heart;
    a first electrode fixed relative to the elongated housing and operatively coupled to the circuitry;
    a second electrode fixed relative to the elongated housing and operatively coupled to the circuitry, the second electrode spaced from the first electrode and positioned along a side wall of the elongated housing;
    a distal extension extending distally from the distal end of the elongated housing, the distal extension defining a lumen extending from a side port proximate a proximal end of the distal extension to a distal opening proximate a distal end of the distal extension and including a distal electrode positioned at distal end thereof and operatively coupled to the circuitry and configured to provide pacing pulses to the Bundle of His; and
    an expandable tubular member releasably coupled to the elongated housing such that the elongated housing is disposed at least partially inside the tubular member, the expandable tubular member having a collapsed configuration for delivery and an expanded configuration that anchors the cardiac device within the patient's vasculature.

2. The cardiac device of claim 1, wherein the distal electrode is slidably and rotatably disposed within the lumen of the distal extension.

3. The cardiac device of claim 1, further comprising an actuator disposed within the lumen of the distal extension and coupled to the distal electrode.

4. The cardiac device of claim 3, wherein the actuator is configured to direct the distal electrode toward a side wall of the patient's vasculature.

5. The cardiac device of claim 1, wherein the distal electrode comprises a helical electrode.

6. The cardiac device of claim 5, wherein the helical electrode is configured to be in contact with the Bundle of His.

7. The cardiac device of claim 1, wherein the distal electrode comprises a curved tine electrode.

8. The cardiac device of claim 7, wherein the curved tine electrode is configured to be in contact with the Bundle of His.

9. The cardiac device of claim 1, wherein the distal extension increases in flexibility from the proximal end to the distal end.

10. The cardiac device of claim 1, further comprising one or more intermediate electrodes positioned on the distal extension at a location proximal to the distal electrode.

11. The cardiac device of claim 1, wherein the expandable tubular member is configured to bring at least one of the first or second electrodes of the housing in contact with a vessel wall.

12. The cardiac device of claim 1, wherein the expandable tubular member is configured to anchor the cardiac device in the patient's superior vena cava proximate the patient's right atrium.

13. The cardiac device of claim 1, wherein the expandable tubular member is configured to anchor the cardiac device in the patient's inferior vena cava proximate the patient's right atrium.

14. The cardiac device of claim 1, wherein the distal extension is configured to extend into the right atrium.

15. The cardiac device of claim 10, wherein the one or more intermediate electrodes are configured to sense atrial events.

16. A cardiac device configured for deployment within a patient's vasculature at a location near the patient's heart, the cardiac device comprising:
    a housing configured to be positioned within the patient's vena cava proximate the patient's right atrium, the elongated housing having a proximal end and a distal end;
    a power source disposed within the elongated housing;
    circuitry disposed within the elongated housing and operatively coupled to the power source, the circuitry configured to pace the patient's heart and/or sense electrical activity of the patient's heart;
    a first electrode fixed relative to the elongated housing and operatively coupled to the circuitry;
    a second electrode fixed relative to the elongated housing and operatively coupled to the circuitry, the second electrode spaced from the first electrode and positioned along a side wall of the elongated housing;
    an expandable tubular member releasably coupled to the elongated housing, the expandable tubular member having a collapsed configuration for delivery and an expanded configuration that locates the cardiac device within the patient's vasculature; and a distal extension extending distally from the distal end of the elongated housing, the distal extension comprising:
  a lumen extending from a side port proximate a proximal end of the distal extension to a distal opening proximate a distal end of the distal extension;
  a distal electrode positioned at distal end thereof and operatively coupled to the circuitry and configured to provide pacing pulses to the Bundle of His; and
  an actuator slidably and rotatably disposed within the lumen of the distal extension and mechanically coupled to the distal electrode, wherein the actuator has a curved end configured to direct the distal ends way from a longitudinal axis of the distal extension when the actuator is distally actuated.

17. The cardiac device of claim 16, wherein the distal electrode comprises a helical electrode.

18. The cardiac device of claim 16, wherein the distal electrode comprises a curved tine electrode.

19. The cardiac device of claim 16, wherein the expandable anchoring device is configured to position a side wall of the elongated housing in contact with a vessel wall.

20. A cardiac device configured for deployment within a patient's vasculature at a location near the patient's heart, the cardiac device comprising:
  a housing configured to be positioned within the patient's vena cava proximate the patient's right atrium, the elongated housing having a proximal end and a distal end;
  a power source disposed within the elongated housing;
  circuitry disposed within the elongated housing and operatively coupled to the power source, the circuitry configured to pace the patient's heart and/or sense electrical activity of the patient's heart;
  a first electrode fixed relative to the elongated housing and operatively coupled to the circuitry;
  a second electrode fixed relative to the elongated housing and operatively coupled to the circuitry, the second electrode spaced from the first electrode and positioned along a side wall of the elongated housing;
  an expandable tubular member releasably coupled to the elongated housing, the expandable tubular member having a collapsed configuration for delivery and an expanded configuration that locates the cardiac device within the patient's vasculature; and
  a distal extension extending distally from the distal end of the elongated housing and configured to be positioned in the right atrium, the distal extension comprising:
    a lumen extending from a side port proximate a proximal end of the distal extension to a distal opening proximate a distal end of the distal extension;
    a distal helical electrode positioned at distal end thereof and operatively coupled to the circuitry and configured to provide pacing pulses to the Bundle of His;
    an intermediate bipolar electrode pair positioned proximal to the distal electrode and configured to sense atrial activity; and
    an actuator slidably and rotatably disposed within the lumen of the distal extension and mechanically coupled to the distal electrode, wherein the actuator has a curved end configured to direct the distal electrode away from a longitudinal axis of the distal extension when the actuator is distally actuated and rotational actuation is configured to twist the distal helical electrode into adjacent tissue.

* * * * *